US012651667B2

(12) United States Patent
Arkoff et al.

(10) Patent No.: US 12,651,667 B2
(45) Date of Patent: Jun. 9, 2026

(54) WEARABLE MEDICAL DEVICE DATA CONNECTIVITY SYSTEM USING LORA

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/053,381

(22) Filed: Feb. 13, 2025

(65) Prior Publication Data

US 2026/0024658 A1 Jan. 22, 2026

Related U.S. Application Data

(63) Continuation-in-part of application No. 18/581,344, filed on Feb. 19, 2024, now abandoned.

(51) Int. Cl.
| | |
|---|---|
| *H04W 4/38* | (2018.01) |
| *A61B 5/00* | (2006.01) |
| *G16H 10/60* | (2018.01) |
| *G16H 40/67* | (2018.01) |
| *H04W 4/30* | (2018.01) |
| *H04W 4/80* | (2018.01) |

(52) U.S. Cl.
CPC ............. *G16H 40/67* (2018.01); *A61B 5/002* (2013.01); *A61B 5/6801* (2013.01); *G16H 10/60* (2018.01); *H04W 4/30* (2018.02); *H04W 4/80* (2018.02)

(58) Field of Classification Search
None
See application file for complete search history.

(56) References Cited

FOREIGN PATENT DOCUMENTS

CN 110197732 A * 9/2019 ............. A61B 5/024

OTHER PUBLICATIONS

Pan, A Remote Health Monitoring System, Method And Device Based On Multi-sensor, Mar. 9, 2029 (Year: 2019).*

* cited by examiner

*Primary Examiner* — Gary Lafontant
(74) *Attorney, Agent, or Firm* — IP Consulting Group; Michael Razavi; Alfred F Hoyte, Jr.

(57) ABSTRACT
The inventive system enables wearables to function as portable, always transmitting medical devices within hospital settings, integrating the data therefrom seamlessly into electronic medical records. The dynamic switching of wearables among virtual Bluetooth hotspots ensures and enhances both the reliability of data transmission and the potential for wearables to contribute meaningfully to the electronic medical record infrastructure within healthcare facilities.

14 Claims, 19 Drawing Sheets

Digital Black
Box Recording   ①

Positive Patient Identification
and
Data Validation   ②

True Source of Data
and Data Export   ③

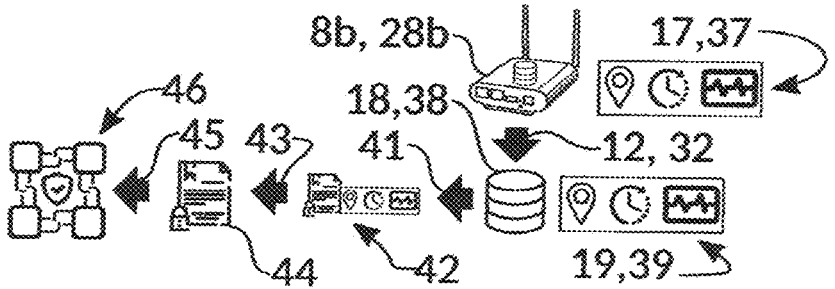
Fig. 5

- BT to Wifi Proxy (tether)
- Direct or Virtualized BT connection via

Complete Process
for Lora Dynamic Mapping
on Each Node

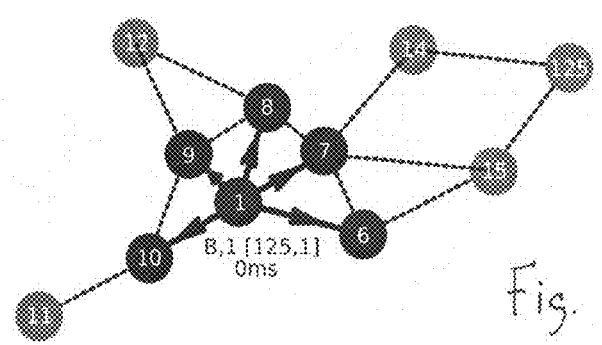

Example of NODE 1 sending to Node 125

STEP 1. Node 1 Broadcast message to 125:
B:1 - [125,1] - 1234 - PAYLOAD

Nodes 6,7,8,9,10 receives nd they decide to
retransmit with following delays:
6 - 25 ms, 7 - 55ms, 8 - 35 ms, 9 - 45 ms,
10 - 25 ms.

Fig. 13A

STEP 2A. Node 6 Broadcast message and
node 15 receives it, 7 receives it and
CANCEL its own proxy broadcast, 1 receives
it and ignores.

STEP 2B. Node 10 Broadcast message and
node 11 receives it, 9 receives it and
CANCEL its own proxy broadcast, 1 receives
it and ignores.

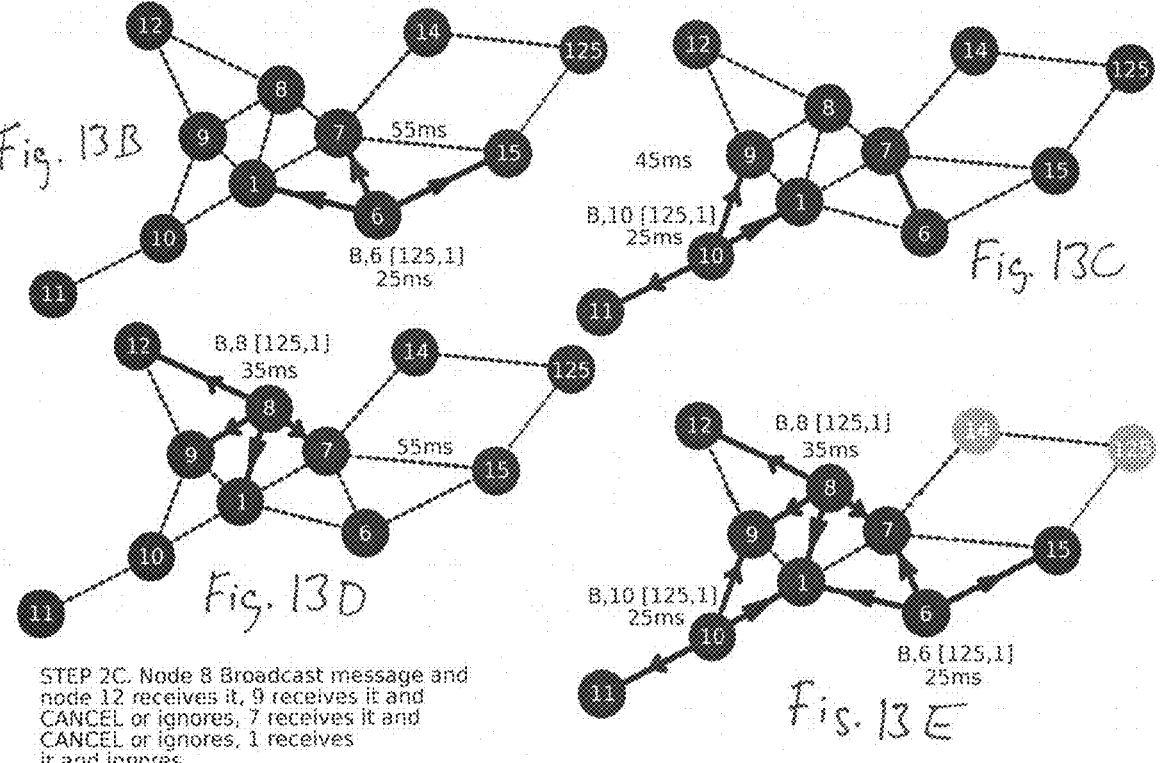

STEP 2C. Node 8 Broadcast message and
node 12 receives it, 9 receives it and
CANCEL or ignores, 7 receives it and
CANCEL or ignores, 1 receives
it and ignores.

STEP 3.
Nodes 11,12 and 15 will start to proxy
the message
and all the nodes received it
(10,9,8,7,and 6)
will ignore it while 125 will send ACK
on step 4.

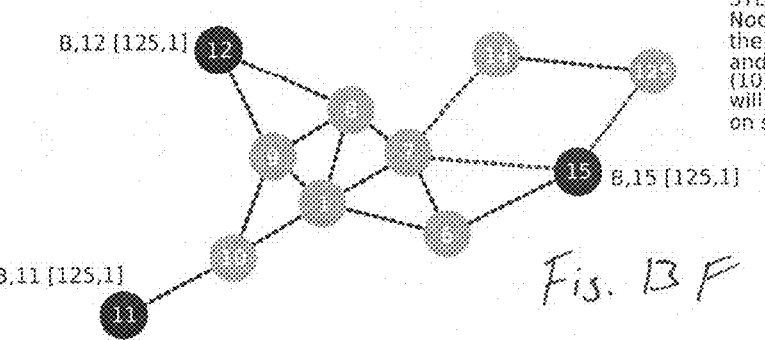

Fig. 13F

Propagation of Dinamic Routing example trough 5 messages.

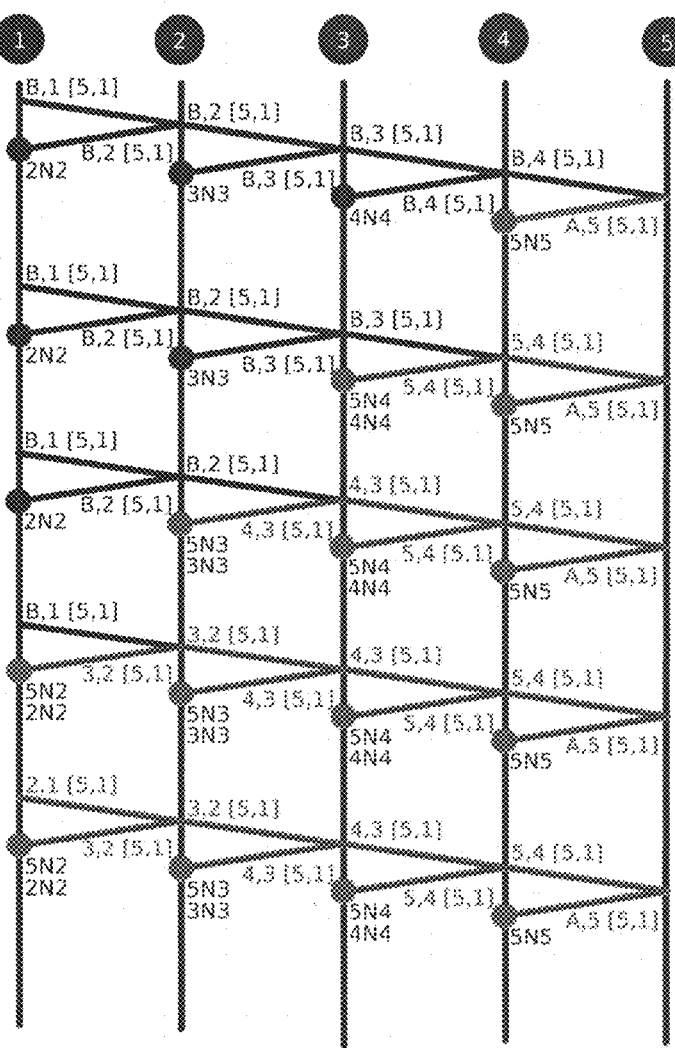

1: [5,1] - sends 4 broadcast messages, last ACK set node 4 to send last message unicast 1: [5,1] - sends 3 broadcast messages, and last unicast. ACK set node 3 to send last unicast for node 5 to 4

1: [5,1] - sends 2 broadcast messages, and last 2 unicast. ACK set node 2 to send last unicast for node 5 to 3

1: [5,1] - sends 1 broadcast messages, and last 3 unicast. ACK set node 1 to send last unicast for node 5 to 2

1: [5,1] - sends only unicast messages, ACK set node 2 to send last unicast for node 1

Fig. 15

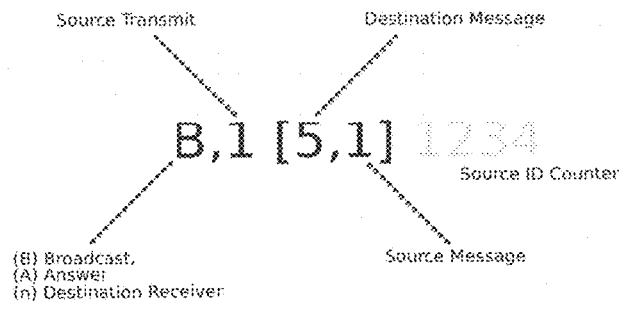

Source Transmit          Destination Message

B,1 [5,1] 1234
Source ID Counter

Source Message (B) Broadcast,
(A) Answer
(n) Destination Receiver

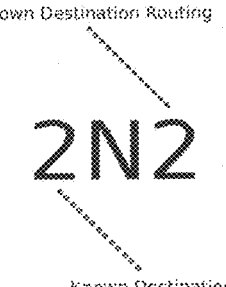

Known Destination Routing

2N2

Known Destination

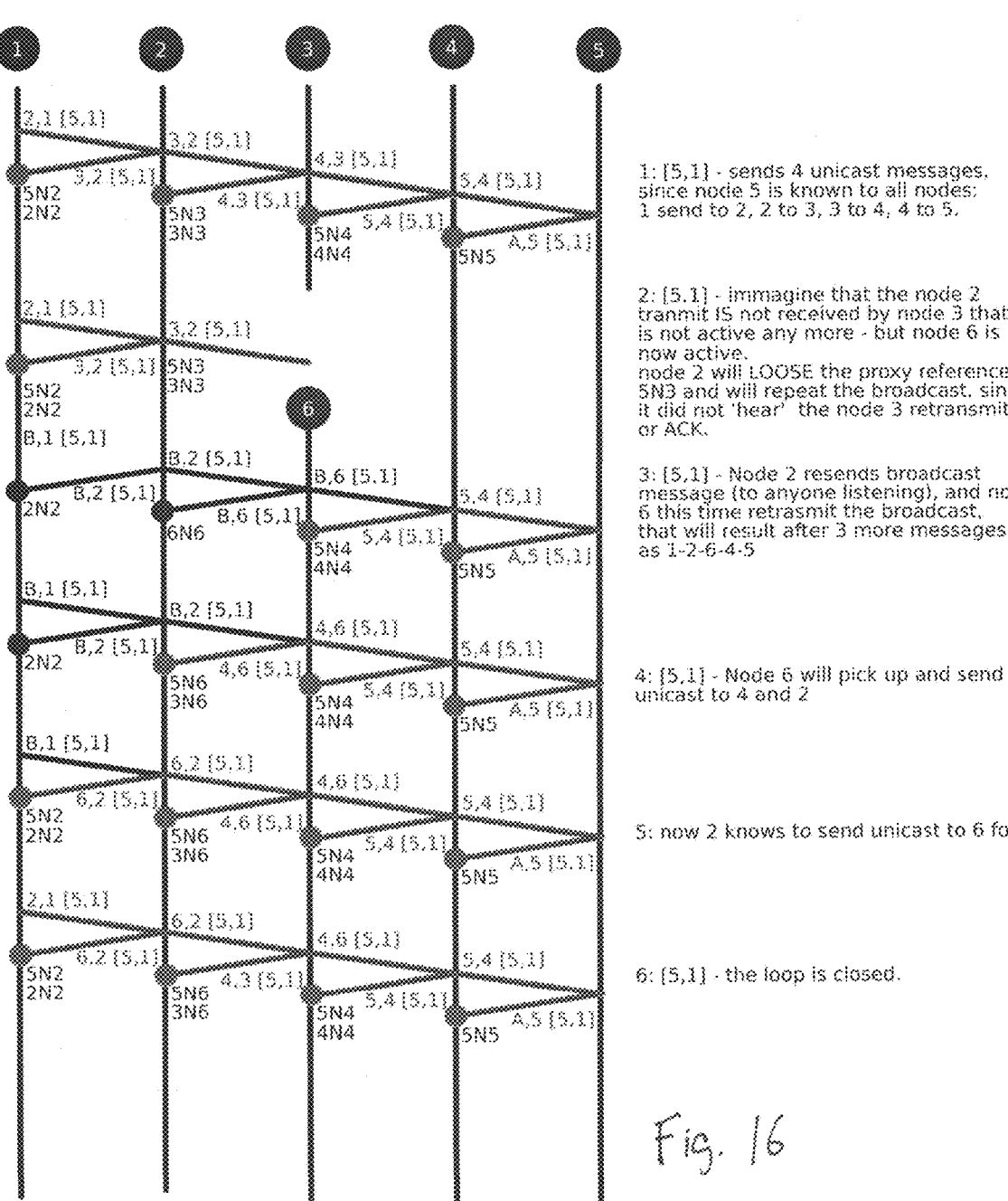

Dynamic Path recreation due to missing node. The node 6 and 3 can both receive and transmit from nodes 2 qand 4.
This situation shows what hapened if node 3 shuts don and si no longer part of the system.

1: [5,1] - sends 4 unicast messages,
since node 5 is known to all nodes:
1 send to 2, 2 to 3, 3 to 4, 4 to 5.

2: [5,1] - immagine that the node 2
tranmit IS not received by node 3 that
is not active any more - but node 6 is
now active.
node 2 will LOOSE the proxy reference
5N3 and will repeat the broadcast. since
it did not 'hear' the node 3 retransmit
or ACK.

3: [5,1] - Node 2 resends broadcast
message (to anyone listening), and node
6 this time retrasmit the broadcast,
that will result after 3 more messages [5,1]
as 1-2-6-4-5

4: [5,1] - Node 6 will pick up and send
unicast to 4 and 2

5: now 2 knows to send unicast to 6 for 5-

6: [5,1] - the loop is closed.

Fig. 16

Dynamic Path preservation on bad (no) receive (or transmit) message

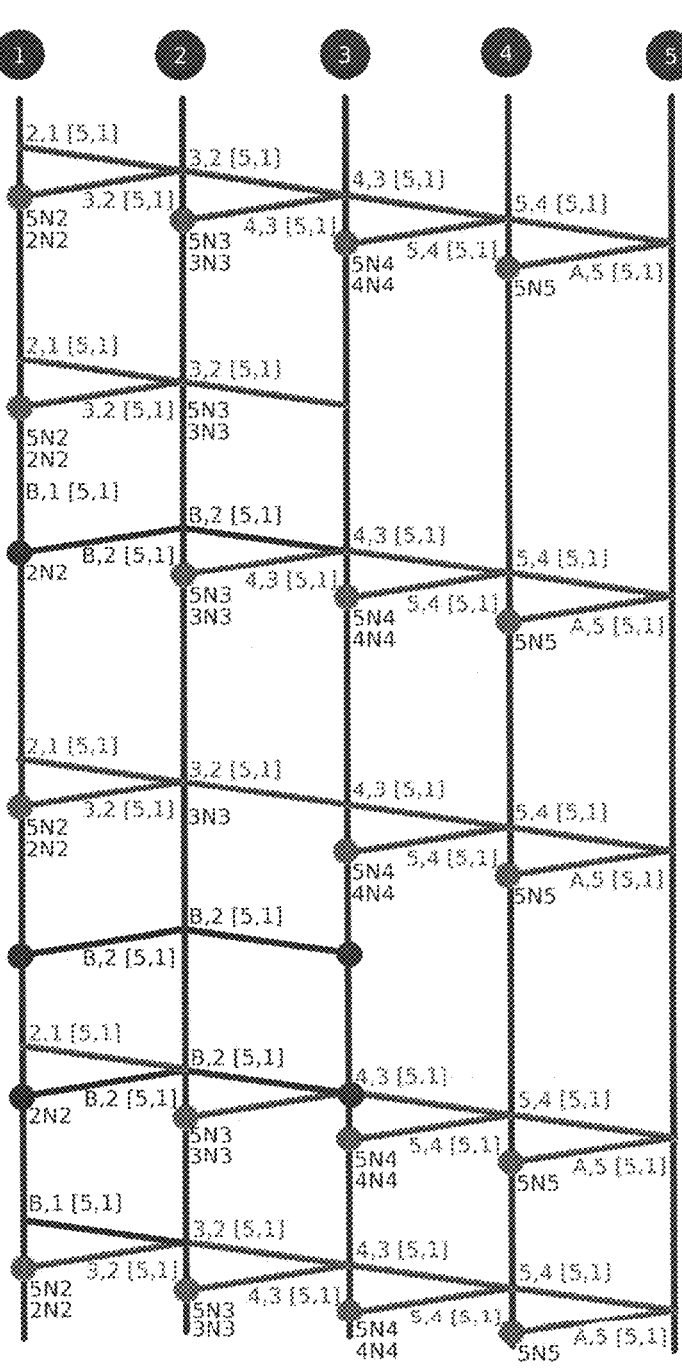

1: [5,1] – sends 4 unicast messages,
since node 5 is known to all nodes:
1 send to 2, 2 to 3, 3 to 4, 4 to 5.

2: [5,1] – imagine that the node 2
tranmit I5 not received by node 3
(but it is by node 1).
node 2 will LOOSE the proxy reference
5N3 and will repeat the broadcast, since
it did not 'hear' the node 3 retransmit
or ACK.

3: [5,1] - Node 2 resends broadcast
message (to anyone listening), and node
3 this time retraismit it and node 2
reconstruct the 5N3 proxy reference.
and reestablish the link.
NOTE - since NODE 3 knows who to proxy
the message, it does not enter in delay
broadcast state, terefore, the dinamic
path will be preserved with more chance
than broken (taken by the next Broadcast
node).

4: [5,1] – imagine that the node 3
tranmit I5 not received by node 2
(but it is by node 4).
node 2 will LOOSE the proxy reference
5N3 and will repeat the broadcast, since
it did not 'hear' the node 3 retransmit
or ACK.

5: But both nodes 3 and 1 will ignore
the repeated broadcast message.

6: [5,1] - next message node 2 will
Broadcast, and node 3 will unicast
the message. so the next time the
node 1 will lose the proxy reference (5N2)
and will...

7: [5,1] - node 1 will broadcast the
message, and reestablish the unic
to node 2 after node 2 will unicast
message to 3 ...

Fig. 17

After a unicast has been disatended, and new Broadcast resent,
only 4 scenarious can happen (A,B,C or D) (other are a sublass of the A,B,C or D):

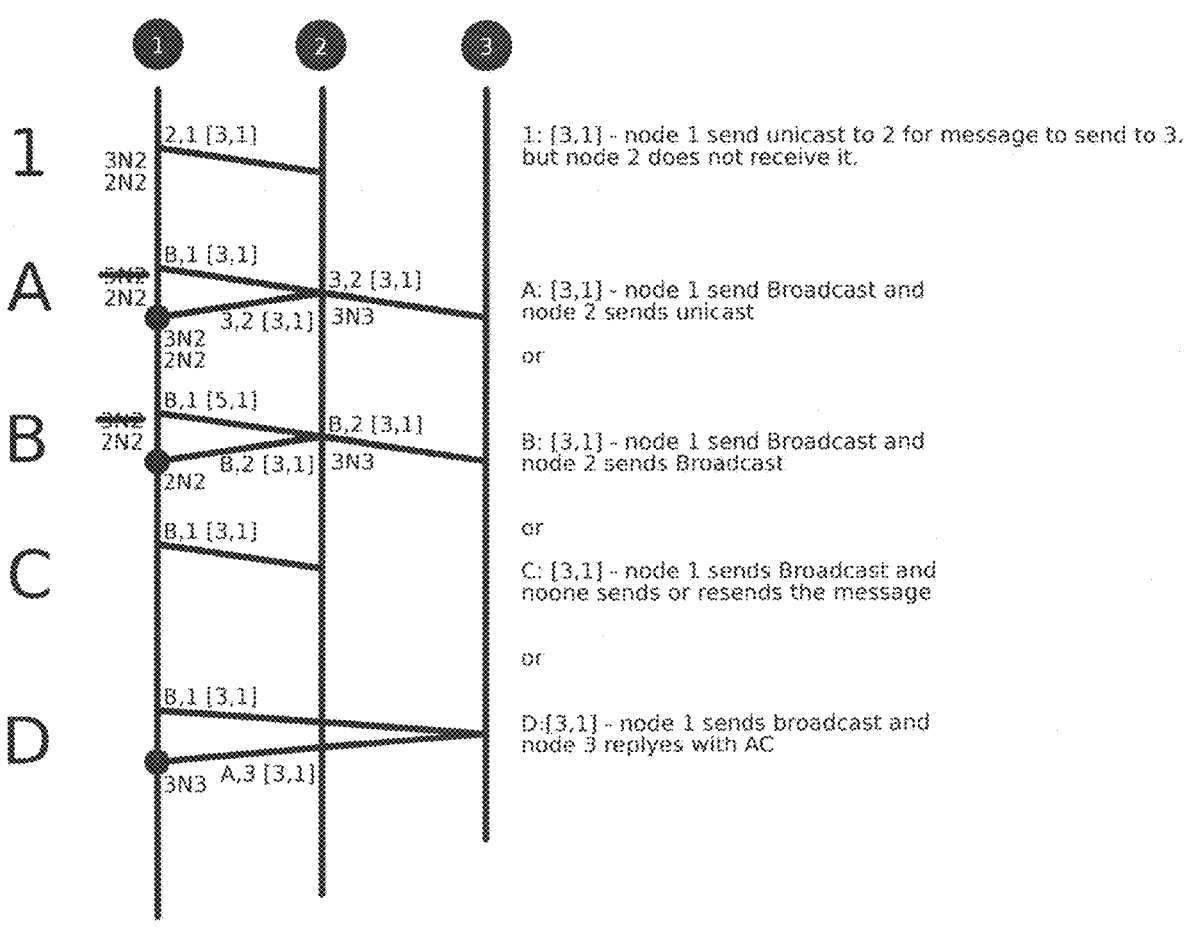

1: [3,1] - node 1 send unicast to 2 for message to send to 3,
but node 2 does not receive it.

A: [3,1] - node 1 send Broadcast and
node 2 sends unicast or

B: [3,1] - node 1 send Broadcast and
node 2 sends Broadcast or

C: [3,1] - node 1 sends Broadcast and
noone sends or resends the message or

D:[3,1] - node 1 sends broadcast and
node 3 replyes with AC

Fig. 18

WEARABLE MEDICAL DEVICE DATA CONNECTIVITY SYSTEM USING LORA

FIELD OF THE INVENTION

This application relates to healthcare data management hardware and software, and more particularly to a reliable method and apparatus for securely connecting medical wearables associated with a mobile patient to data monitoring and storage hardware from within or without a healthcare facility.

BACKGROUND

Modem hospitals are complex, technologically sophisticated organizations having sometimes thousands of employees, doctors, nurses, medical technicians, and administrators, with critical life or death decisions being made regularly and sometimes having to be made abruptly and quickly. Up-to-date, perspicuous, and complete data about the patient can make a difference.

And even when critical decisions are not at stake, increases in the cost of health care have made it imperative to optimize use of hospital resources and facility personnel. More importantly, the need to minimize adverse events and medical errors by providing hospital personnel with remote access to real-time patient data.

Patient wearables, that is, medical devices that monitor various aspects of a patient's health such as heart rate, rhythm, temperature, blood pressure and glucose monitoring are increasingly being used outside of the hospital for personal use, but not routinely being used in hospitals and other patient care facilities for lack of infrastructure to integrate into hospital information systems and workflow.

Wearables are typically designed to only communicate to an individual's personal smartphone via Bluetooth. Wearables have not been designed to communicate with the data infrastructure in hospitals, prohibiting their widespread adoption for use in hospitalized patients. Efficiently collecting data from wearables allows the data therefrom to be more easily integrated into a Medical Data Governance system as described herein.

Accordingly, it would be beneficial to provide a method and apparatus to allow a patient with wearables to roam within or outside a facility, while continuing to transmit data from the wearable to the appropriate storage/processing facility.

SUMMARY

In accordance with the present disclosure, embodiments of a system, method, and apparatus are described which eliminate or ameliorate the problems and disadvantages associated with previous systems, methods, and apparatuses.

Due to the exponential data availability from growing health-related devices, the risk of data not being collected, or worse, being wrongly associated, grows exponentially. In a particular embodiment, the present invention opposes this trend by allowing a patient with a wearable to roam within a facility and continually transmit data in a secure and seamless fashion.

The instant invention provides a simple, stress-free connection and data transmitting scheme for patient wearables requiring no special effort on the patient or hospital staff.

The instant invention provides a method to optimize patient monitoring by utilizing every computing device within a facility or predetermined area as Bluetooth hotspots actively seeking known medical devices. These computing devices act as virtual intelligent routers, continuously searching for and switching wearable devices among them to achieve the best Bluetooth signal strength and ensure the seamless continuity of data from the patient. The inventive system enables wearables to function as portable, always transmitting medical devices within hospital settings, integrating the data therefrom seamlessly into electronic medical records. The dynamic switching of wearables among virtual Bluetooth hotspots ensures and enhances both the reliability of data transmission and the potential for wearables to contribute meaningfully to the electronic medical record infrastructure within healthcare facilities.

The instant invention provides a simple, stress-free connection and data transmitting scheme for patient wearables associated with a patient requiring no special effort on the patient or hospital staff which uses a mobile phone that is not associated with a patient to provide connectivity to facilitate roaming within or outside a facility.

The instant invention provides a simple, stress-free connection and data transmitting scheme for patients which uses a mobile phone to facilitate roaming within or outside a facility, by using the fingerprint of a Bluetooth descriptor connected to the IoMT hub with a mobile phone.

BRIEF DESCRIPTION OF THE DRAWINGS

For a more complete understanding of the present disclosure and its advantages, reference is now made to the following description taken in conjunction with the accompanying drawings, in which like reference numerals represent like parts.

FIG. 5 is an illustration of the details of providing block chain signatures for black box recorded patient data sets in an embodiment.

FIGS. 13A-13F illustrates a transmission scenario in the LoRa network of the invention.

FIGS. 15-18 illustrate various connectivity scenarios in the LoRa network of the invention.

DETAILED DESCRIPTION

The present invention concerns a method and apparatus for obtaining data from patient wearables, and ultimately exporting the data to an EMR using the MDGS as herein described. More specifically, the invention allows for patient mobility within or outside any healthcare facility that has an existing medical data governance (MDG) system in place. The invention is a Bluetooth virtual proxy network comprised of multiple Bluetooth computing devices. When using multiple proxy computing devices together we have created a virtual distributed network of Bluetooth proxy computing devices that become virtual intelligent routers. The real-world application is that a patient can roam within or outside a facility and relay the data from their wearable back to bedside MDDS units via any computing devices in the facility with a Bluetooth receiver running the inventive proxy software service. The proxy computing devices can be the patient's personal smartphone or phone, a nearby smartphone from an employee or any computer in the facility that is running this proxy software service. It should be noted that the terms phone and smartphone are used interchangeably throughout the discussion, both terms referring to a phone device that can be digitally networked via, e.g., the internet, WLAN, LAN, etc. These all work together collectively as a MESH network. In accordance with the method of the instant invention, instead of using Bluetooth API of the hardware (the industry standard and custom) by which wearable device data is acquired, stored, analyzed, displayed, and sent to the storage system, these functionalities are virtualized on the host and not the hardware (the phone or the computer). Algorithm processing is not performed on the hardware. The hardware is used only as a relay to acquire the data and the processing occurs on the MDDS units. There is only one footprint for all wearables. Instead of one application for each wearable a patient uses, there is only one application for all wearables. In the inventive scheme, the wearables need not be paired with the patient's phone, although this is an option as will be discussed below.

Figure 1:
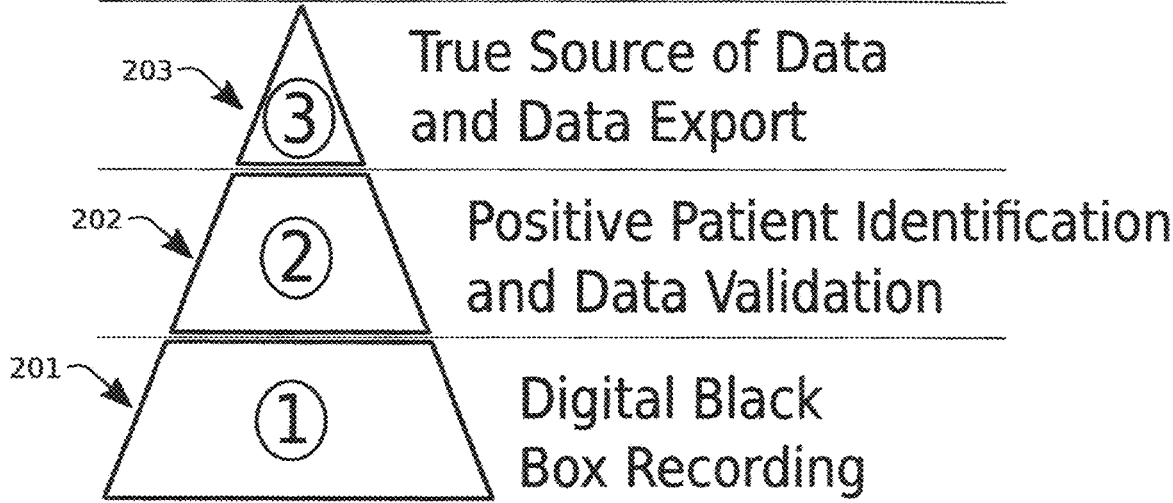
FIG. 1 is a block diagram overview of a Medical Data Governance System.

FIG. 1 is a block diagram overview of the three functional layers of a Medical Data Governance System (MDGS) in an embodiment. The base layer 201 is a digital black box recording of patient data. The middle layer 202 is positive patient identification and data validation. The top layer 203 is true source data and data export for research and other purposes.

Binding Location (geo-localization, indoor localization), Time, Provider, Patient is associated with data obtained from isolated or networked medical and medical relevant devices. The MDGS collects the data from medical devices such as wearables, identifies them, normalizes and time synchronizes all the data outputs while storing them safely, with tamper detection methods (such as blockchain) local to the source of data. Partial and/or metadata about the collected data are used to identify the related patient, patient location, patient provider, source of data and location from whom the data had been collected when available. In the process described as MDGS, the normalized data along with time, time span, location, patient are securely stored and saved for data export into third party systems (data consumers) or stored for later export. The process of binding Location, Time, Provider, Patient to the data can occur pre or post data collection, generating new datasets at each intervention or association, creating incremental dataset groups. For example, complete patient association can be done hours or days after the data has been collected, as well as preset before the data is collected from the medical device.

Patient Treatment Time Optimization and Device Asset Management

MDG provides a true source of data that can highlight the schedule time variations of exams and other medical treatments and provides tools for the rescheduling feedback, contacting and receiving feedback from patients/physician/healthcare professionals thus introducing general system flexibility through the use of lean process and six sigma methods. MDG leverages modern communication methods (phone applications, emails, web services . . . ) and easily links patient and physician/other healthcare professionals to the scheduled use of medical devices. After unexpected events that may cause a miss in scheduled operations, the MDG may create a backup schedule to preemptively fill the gaps and may facilitate healthcare and schedule professionals to optimize machine time usage. This could create a new marketplace for priority services for those patients that opt for it.

Patient/User Data Monetization by Patient/User, Institution, or Combination Thereof MDG enables patients/users and/or Institutions to monetize their vitals, medically relevant data, and other patient data collected during the stay inside the healthcare institution, as well through the extended data collected over a period of time in multiple stays or spot measurements in healthcare institutions. Patients and/or Hospitals could establish a relationship with a third party (such as a drug manufacturer, independent drug trials projects, undisclosed trials to the institution) and provide to the third party normalized data collected, organized, and provided by the MDG used by the healthcare institution, and provided to the patient in different standardized formats, even in near real time. The institution might not be aware of the final user of the patient data. MDG can create additional revenue to the institution by monetizing such a service per patient and per data processed. MDG can track and trace data usage per patient and assets. MDG through the export of all specific, validated clinical data, medical relevant data, could create a new data-based economy. Third parties (researchers or corporations) could establish a relationship with individuals and hospitals to provide data through a Federated System for the purpose of research, development, and regulatory approval of new medical grade wearables.

Patient Notification and Pre or Post Consent of Data Use for Second Opinions, Medical Treatments, Specific Research, Validation, Education, or Application.

MDG is solving the problem of giving consent and approval, or notification for use of the patient data for second opinion, medical treatments, specific research, validation projects, and educational purposes. Specific patient or user data is previously screened based on always updated, public, generic, anonymous metadata (for example: sex, age, days in hospital, normalized data content and length: heart rate, respiration rate, drugs, etc.).

Research Dataset Optimization

MDG allows for third party statistical analysis (research) on the whole population dataset, without exporting or providing data to the third party, but rather comparing the result to the legally available consent subset group. A statistically relevant result might indicate a minimal group of statistically significant subset of data to search consent and optimize the time for valid and repeatable dataset.

Data Normalization

Data normalization appears to be a key element for application of Artificial Intelligence in Healthcare. MDG, through the acquisition of higher frequency (sub-minute/sub-seconds), high fidelity data, patient identification, provider identification, data validation, time synchronization, localization of different, non-homogeneous clinical, medical relevant, patient relevant data from isolated, standalone medical devices or networked devices, can provide a superior, in terms of quality and quantity, subset of normalized data.

Metadata

MDG collects, stores, normalizes, and time synchronizes all available data points from any patient related source of data. Metadata such as healthcare provider, environment temperature, hours of operation of medical device, time from last service, related errors can provide almost endless sources of data for future use or research.

An Overall Solution to the Lack of Standards and Interoperability

MDG, as a sole purpose of true source of data, and without any specific end user purpose serves as an interoperability and standardization tool, enabling the health industry to leverage stored data through new and old standards based on the need.

Root-Cause Analysis and Continuous Quality Improvement (CQI) Classification

As a most complete data gathering and presentation tool, any adverse case or event can be studied up to the maximum details recorded by the MDG for Root Cause Analysis in cases of Morbidity and Mortality within a healthcare facility. MDG tools help in retrieving patient identification, provider identification, data validation, time synchronization, localization of different, non-homogeneous clinical, medical, medically relevant, patient relevant data after adverse events, providing tools for analyzing risks, therefore introducing quality, process, outcome improvements. This classifies MDG as a quality improvement tool, therefore protected from legal perspective to be used as proof of malpractice or errors. Non-medical user notification and pre or post consent of data use for specific research, validation, education, marketing, or application. The ability of handling critical data can be extended to several personal user data in different fields outside of medical applications, like sports, fitness, and general health.

Figure 2:
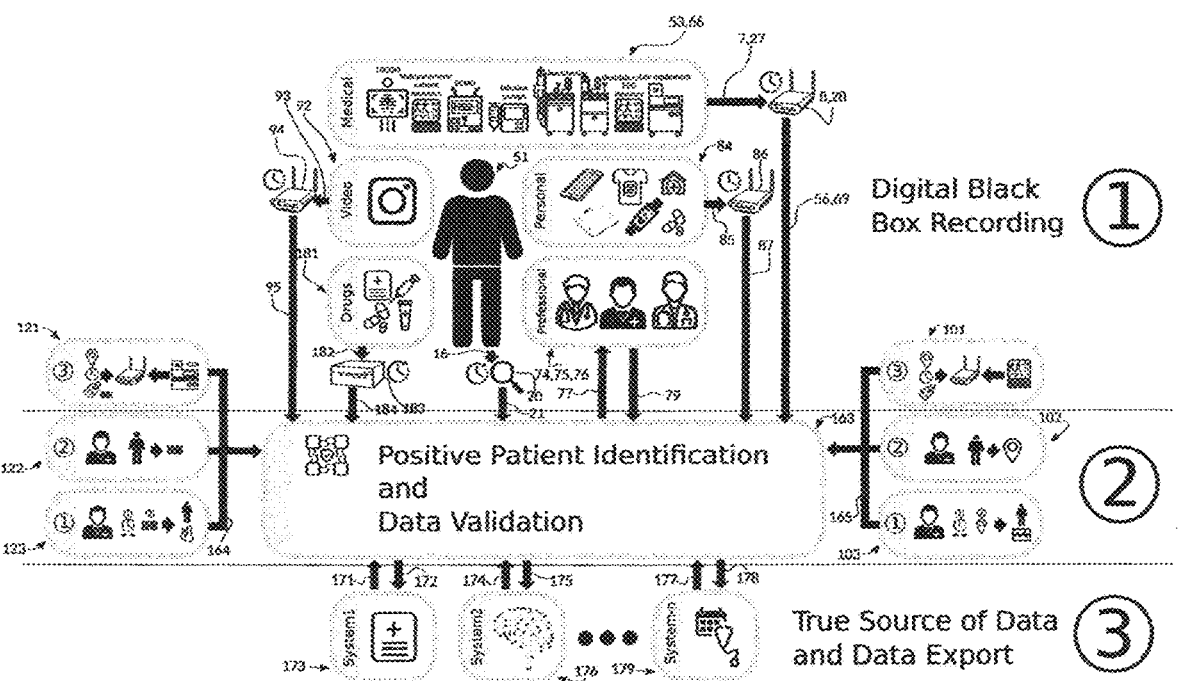
FIG. 2 is an illustration providing high-level detail about each layer of the MDGS pyramid of FIG. 1.

FIG. 2 is an illustration of a simplified 3-layer MDGS in an embodiment. Artificial Intelligence, Machine Learning systems, and Deep Learning Systems all require a medical data governance middleware to assure proper, normalized and verified data inputs. Legacy health information systems and electronic medical records (EMR) were designed to receive only a minute portion of the exponentially increasing data medical devices can create and can be collected. Also, outdated HIS/EMR (Healthcare Information Systems/Electronic Medical Record) and inadequate patient identification and association can cause serious errors in the future of precision medicine, augmented intelligence, and AI, as well as representing a serious bottleneck for data-hungry personalized medicine, real time applications, and in practice, most medical device data are not recorded at all.

Layer (1): Black Box Recording

Data from hospital medical devices, continuous monitoring systems and laboratory devices 53, 66, through the use of proper physical and software drivers 7, 27 are collected by Medical Device Data System (MDDS) devices 8, 28 and location/time synchronized, optionally signed with block-chain service, and made available to the second layer of the MDGS—Positive Patient Identification and Data Validation. Medical Device Data Systems (MDDS) are hardware or software products intended to transfer, store, convert the format of, or display medical device data. A MDDS does not otherwise modify the data or its display, and it does not by itself control the functions or parameters of any other medical device.

Similar to laboratory devices, video 92 can be transferred 93, recorded 94, location/time synchronized, and then transferred when convenient 95 to a central repository and patient locked by the second layer. Wearables and home or community care data and sensors 84, generally available through BLE (Blue Tooth Low Energy, BT4.1) wireless protocol 85, can be registered and time synchronized by a portable MDDS device or phone application 86, and available or optionally transferred 87, when possible, to a central repository.

Professional notes, comments, orders, and communications, generally known as Journaling, 74, 76 can be tracked, reported, and stored 77, 79 via third party systems and solutions.

Drug Distribution, Administration and all other third-party software and systems 181, 182, 183 can be tracked, tagged, stored, time synchronized and made available 184 to the third layer.

Each MDDS has a location 101 and metadata configuration panel available for setup 121 so the medical device data can be location or patient tagged for patient data association and data validation.

Layer (2): Positive Patient Identification (PPI) and Data Validation (DV)

As described below in more detail in the description of FIG. 5, PPI and DV depends on previous location and metadata setup of MDDS 121, 101 (FIG. 2) and proper data entry of metadata 122 or location 102, and active healthcare professional confirmation of patient location time presence 103 or the proper patient identification process 123. Upon PPI and DV, different segments of Digital Black Box recordings are patient and time segment tagged 163 and available to the third layer, True Source of Data and Data Export.

Layer (3): True Source of Data and Data Export

By concentrating all available medical relevant data into a single source and providing a subset of data to each receiving sub-system 173, 176, 179 with the correct source and time reference, the Medical Data Governance System becomes the True Source of Data and guarantees the data consistency through the use of block chain signatures.

Due to the exponential data availability from growing health-related devices, the risk of data not being collected, or worse, being wrongly associated, grows exponentially. The MDGS opposes this trend by using the same data to augment the data affinity and isolate and indicate possible association or data integrity errors.

The MDGS, as the True and Complete Source of Data, should be used as the front end for sub-systems. When errors are detected from automated systems or from a later check or evidence, errors are propagated through related data, and when the data, a wrong association or time reference is corrected and signed with block-chain, the whole time segment of the data must be resent to the sub-system rather than those subsystems being corrected independently.

Each medical subsystem 173, 176, 179 is designed to receive specific data with a specific frequency, quantity, and quality. Sometimes the specific data, frequency, quantity, and quality do not overlap between subsystems. From the Complete True Source of Data, the specific export drivers

171, 172, 174, 175, 177, 178 collect, filter, consistency check, transform and deliver appropriate data to each subsystem.

Figure 3:
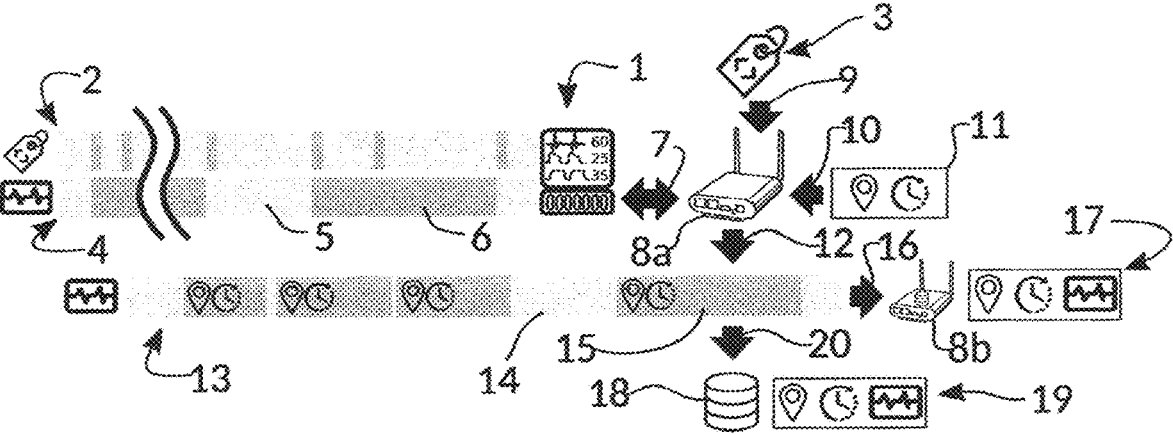
FIG. 3 is an illustration of the details of continuous patient monitoring measurement, part of the first layer of MDGS, Digital Black Box Recording, in an embodiment.

FIG. 3 is a block diagram illustrating details of one component of Layer (1) Digital Black Box Recording, in particular, the medical devices that measure continuous patient data, such as Multiparametric Patient Monitoring, Anesthesia machines, EEG and similar belonging to the "continuous" group of potentially retrievable medical data 4, where the session beginning, duration and therefore, its end can be associated using continuous, complete data flow without data interruption 6. Previous idle, non-patient data that is irrelevant and does not provide any information, except the fact that at that time patient data was not being collected is noted 5. Metadata such as device not ready, cable disconnected, device powered off is recorded 2, including but not limited to room temperature and pressure, video, and other environment data if and when available such as other medical devices connected 3 that provide essential information about the start and stop of the data valid session 6. Medical devices 1 usually have one or more data export mechanisms 7 which are used by a Medical Device Data Systems (MDDS) unit 8*a* to extract and collect ALL possible data, along with metadata 2, 3 from specific software and hardware drivers and interfaces 9 and along with previously associated 10 location, metadata and clock-time 11 reference.

The MDDS unit 8*a*, which is a patient bedside unit associated with a particular patient as discussed in more detail below, stores 16 location sessions 15 with all medical data collected, metadata, timestamps and location identifiers 13 and keeps it for a limited time, for example up to 24 hours, before it copies it 20 to a centralized repository 18. Empty, non-relevant data 14 are simply not propagated and ignored.

The MDDS 8*b* can serve a complete time synchronized and location subset of near real time data 17 without intermediary subsystems, or if the complete dataset had been copied to a centralized repository 18, the past data subset 19 can be retrieved from the repository services 18.

Figure 4:
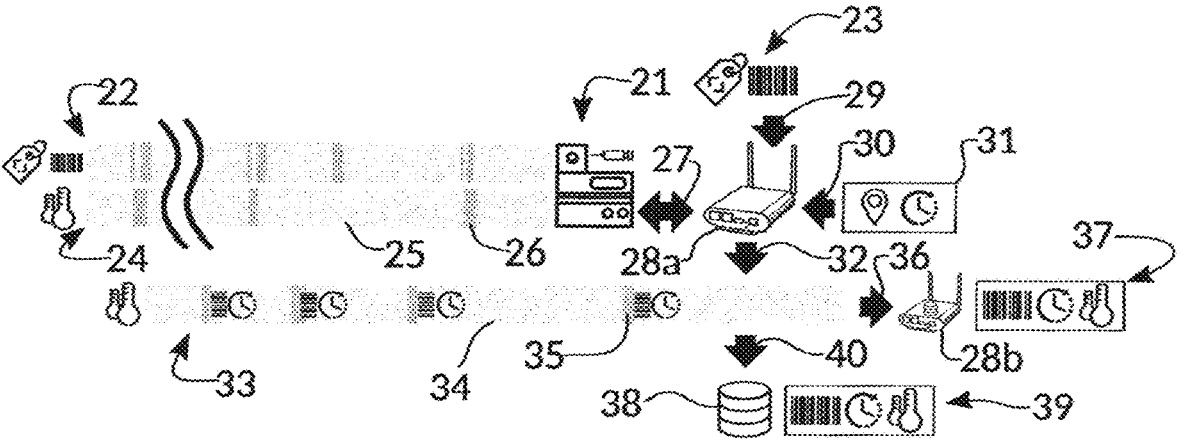
FIG. 4 is an illustration of the details of the recording of sporadic patient related data, part of the first layer of a MDGS, Digital Black Box Recording, in an embodiment.

FIG. 4 is a block diagram illustrating details of another component of Layer (1) Digital Black Box Recording, in particular, medical devices that measure sporadic patient related data 21 such as Blood Gas Laboratory Machines, Generic Laboratory Devices, Portable Non-Invasive Blood Pressure devices, Scales and similar belonging to the "spot" group of potentially retrievable medical data 24. The session beginning, duration and result can be directly associated from meta-data, such as bar code patient ID, Point Of Care (POC) input, and the result 26. Previous idle, non-patient data that is irrelevant and does not provide any information is not propagated, except for the metadata indicating that at that time patient data results were not being collected 25. Metadata is included such as, but not limited to, Patient Bar Code ID, POC input, device not ready, cable disconnected, device powered off 2, but also room temperature and pressure, video, and other environment data such as other medical devices connected 3 that provide essential information about the start and end of the result data 26. Medical devices and Laboratory devices 21 usually have one or more data export mechanisms 27 which are used by a Medical Device Data Systems (MDDS) 28*a* to extract and collect ALL possible data, along with Metadata 22, 23 from specific software and hardware drivers and interfaces 29 and along with previously associated 30 location, metadata and clock-time reference 31.

The MDDS stores 36 location sessions 35 with all medical data collected, metadata, timestamps, and location identifiers 33 and keeps it for a limited time, for example up to 24 hours, before it copies it 40 to a centralized repository 38. Empty, non-relevant data 34 are simply not propagated and are ignored.

The MDDS can serve a complete time synchronized and location subset of near real time data 37 without intermediary subsystem, or if the complete dataset had been copied to a centralized repository 38, the past data 39 subset can be retrieved from that repository service 38.

In any case, the Layer (1) Digital Black Box Recording does not have Protected Health Information (PHI), and if it is provided, it is stripped off and eliminated from the stored data. The possible PHI is removed from drivers handling specific medical devices.

Blockchain in Signature Anti Tampering Protection

When the MDDS 8*b*, 28*b* transfers the complete time synchronized and location data set 17, 37 to a centralized repository 18, 38, then as depicted in FIG. 5, the past data set 19, 39 is "signed" 41, 42, and the Signature 44 is produced 43. The signature can be transferred 45 or stored to the external Block Chain Server Authority 46 to tamper proof the data collected and have an external safety check for data consistency.

Figure 6:
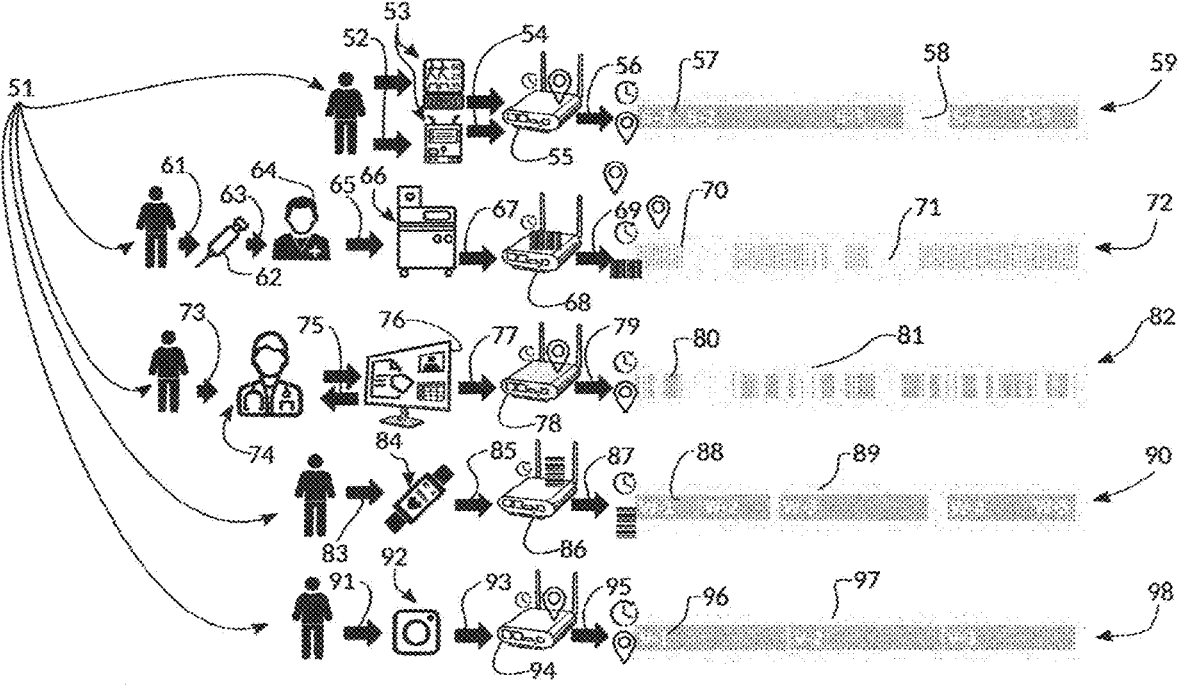
FIG. 6 is an illustration of the details of a black box recording of a variety of different types of patient data in an embodiment.

Electronic Black Box Recording Data Diagrams for Various Medical Data and Medical Relevant Data Sources Different medical and medical relevant data types are recorded, including location and patient ID metadata, and time synchronized with medical device data as depicted in FIG. 6. Continuous medical devices 59, laboratory devices 72, professional journaling and comments 82, personal wearables and fitness trackers 90, and video capture systems 98 store the non PHI (Protected Healthcare Information) only.

Continuous Medical Measurements 59

When patients 51 are connected with physical sensors and/or leads 52 to medical devices 53 that have the capability to export real or near real time data 54 to an MDDS 55, the MDDS 55 will timestamp, location and metadata associate the data created 56 with a Digital Black Box Recorder dataset 59 consisting of different data sessions 57 and idle time 58.

Laboratory Data 72

Samples of blood or other patient relevant organic samples 61 are taken and temporary conserved 62 and transported 63 by healthcare professionals 64 then properly processed and electronically identified 65 by laboratory device 66. The lab equipment should have the ability to export metadata such as POC or ID-collected and lab results in an electronic format 67 which is collected and processed by the MDDS 68. The MDDS will timestamp, location, ID and metadata associate the data creating 69 a Digital Black Box Recorder dataset 72 consisting of different laboratory results 70, metadata of patient identification codes and idle time 71. Protected Healthcare Information is stripped off and assure the data to be deidentified matching a single universal identification code to be stored instead if not already provided.

Medical Journaling 82

Every patient 51 consult, visit or opinion 73 between patient 51 and the medical professional 74 can be recorded or have notes taken 75 by third party software or systems 76 and directly exported or queried 77 from the MDDS 78 systems at the place of creation (near the patient current location). The MDDS will timestamp, location, ID and metadata associate the data, creating 79 a Digital Black Box Recorder dataset 82 consisting of various notes and documents, video, and audio notes 80, metadata of patient identification codes and idle time 81. Protected Healthcare Information will be stripped off and ensure the data is deidentified matching a single universal identification code to be stored instead.

Wearables and Fitness Trackers 90

Patient 51 might have 83 various personal wearable devices operating with BLE (blue tooth low energy or similar technologies) 84 that can be periodically or constantly in communication 85 with a fixed or portable MDDS or smartphone MDDS app 86 (see FIG. 6) that has been preprogramed with a constantly updated Bluetooth fingerprint or Bluetooth descriptor such as a BLE MAC address, unique identifier code, or serial number to receive and associate the medical devices with the patient. Like the continuous medical measuring 59 and the measure-result laboratory systems 72, data sessions are defined 87 with metadata such as Bluetooth descriptor, patient location, and non-relevant data segments 89. However, with a fixed MDDS such as 8b, 28b, the patient 51 cannot roam within the facility without going out of range of the MDDS. Accordingly, in an embodiment of the invention, a method is provided to allow a patient to roam within a facility while allowing continuous transmission of data from wearables, as will be discussed in more detail below.

Video and Medical Relevant Data 98

Referring now particularly to FIG. 6, all patient 51 relevant video or medically relevant ambient data 92 can be recorded 93, time and location synchronized by the MDDS 94 system. The MDDS 94 will timestamp, location, and metadata associate the video and/or ambient data creating 95 a Digital Black Box Recorder video or ambient dataset 98 consisting of different data session 96 and idle time 97.

Figure 7:
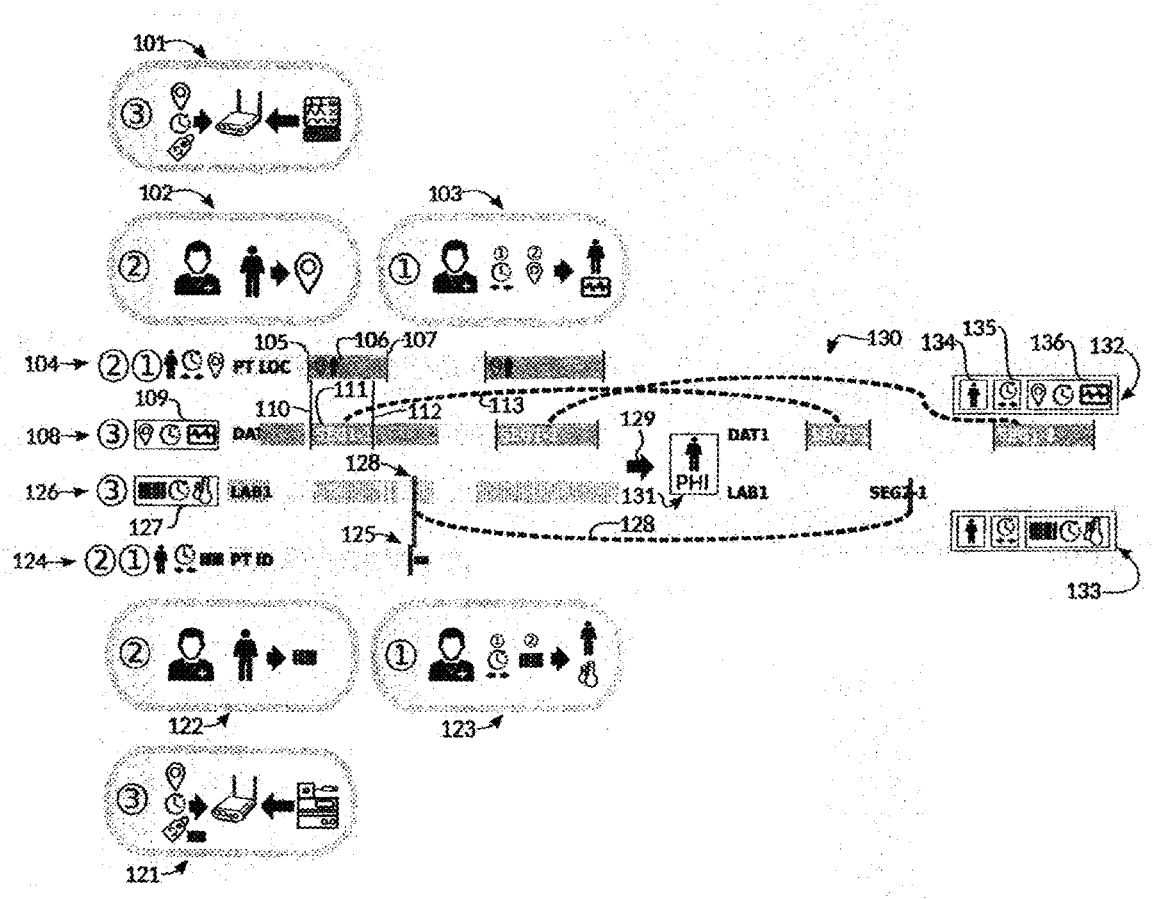
FIG. 7 is an illustration of the details of the second layer of a MDGS, Positive Patient Identification and Data Verification in an embodiment.

Second Layer of Medical Data Governance: Positive Patient Identification and Data Validation FIG. 7 shows the process of association between the patient and the data collected from, e.g., a wearable, or to be collected 101, 121. An external process, software, or system associates a Patient Identification code to a location 102 or patient-to-patient Identification code 122. An active healthcare professional, or someone that has been assigned to verify the patient data, patient location or patient identification, confirms the three key elements of the patient data triplets: patient identification and its code 134, segment, or segments of time the patient was on location 135, and patient data collected at that location 109, 136 throughout the active process 103, 123.

Due to patient location recorded or provided by third party systems 102, 104 and data and metadata collected 101, 108, a subsection defined by start 105 and stop time 107, identified by a healthcare professional 106 or by third-party systems allows the precise selection of the appropriate and consistent data session 111 and seamlessly finetunes the accurate start 110 and stop 112 of the particular data session 113, then creates the building block of triplets 132 that constitutes a complete positive patient identification and data validation record 130.

For a laboratory, or multi patient systems such as laboratory machines, an action that immediately precedes or clearly relates to the result being consecutively transferred and collected by the MDDS system 121, a previously created Patient Identification code 122 is collected as metadata and time synchronized with the result that is collected. An active process of confirming the data 128, patient and patient id 125, and validity of test result 123 creates the triplets 133 from the data set recorded 126 and the patient, time segment and location information 124.

Protected Healthcare Information and Anti Tampering with Block Chain Signature

Figure 8:
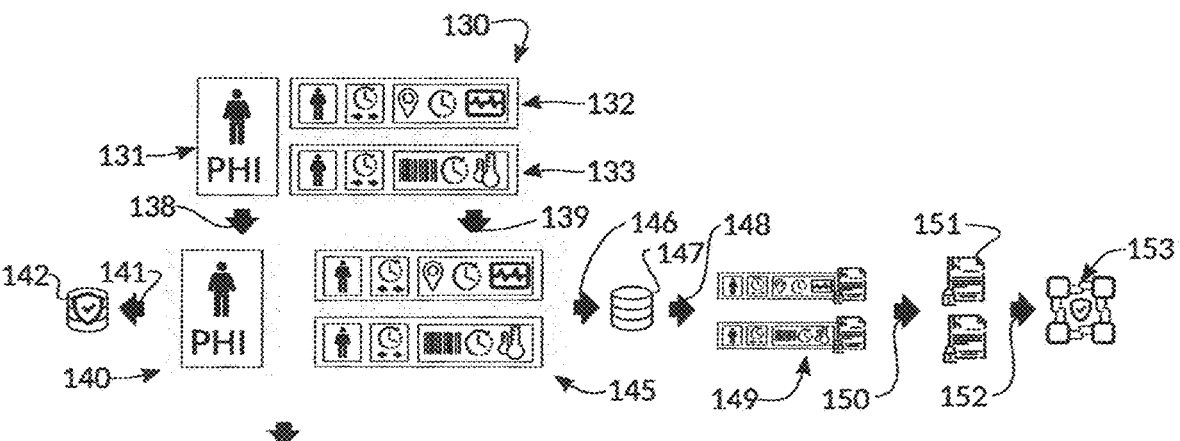
FIG. 8 is an illustration of the details of the process of storing Protected Healthcare Information (PHI) and providing a PHI data set with a block chain signature.

As depicted in FIG. 8, the process of active Positive Patient Identification and Data Validation creates multiple patient time segment data records 132, 133 associated with the patient 130 where PHI is shown, visible 131 and essential for positive patient association and the data validation process. After the modification of the previous data segments due to different information such as different times or location association, or upon creation of new triplets, they are stored 139 separately 145 from the storing 138 of the PHI 131. PHI 131 is stored 138 on third party systems 140, 141 running on a protected database system 142.

Upon confirmation of the triplet's association 145, each triplet is recorded 146 on a database 147 that triggers an automatic digital signature of each record 149 and a signature certificate is transferred 150, 151 and delivered 152 to the third-party Block Chain system 153 for safety and anti-tamper proofing of the data.

Medical Data Outputs and Deidentified Research Data Exports

Figure 9:
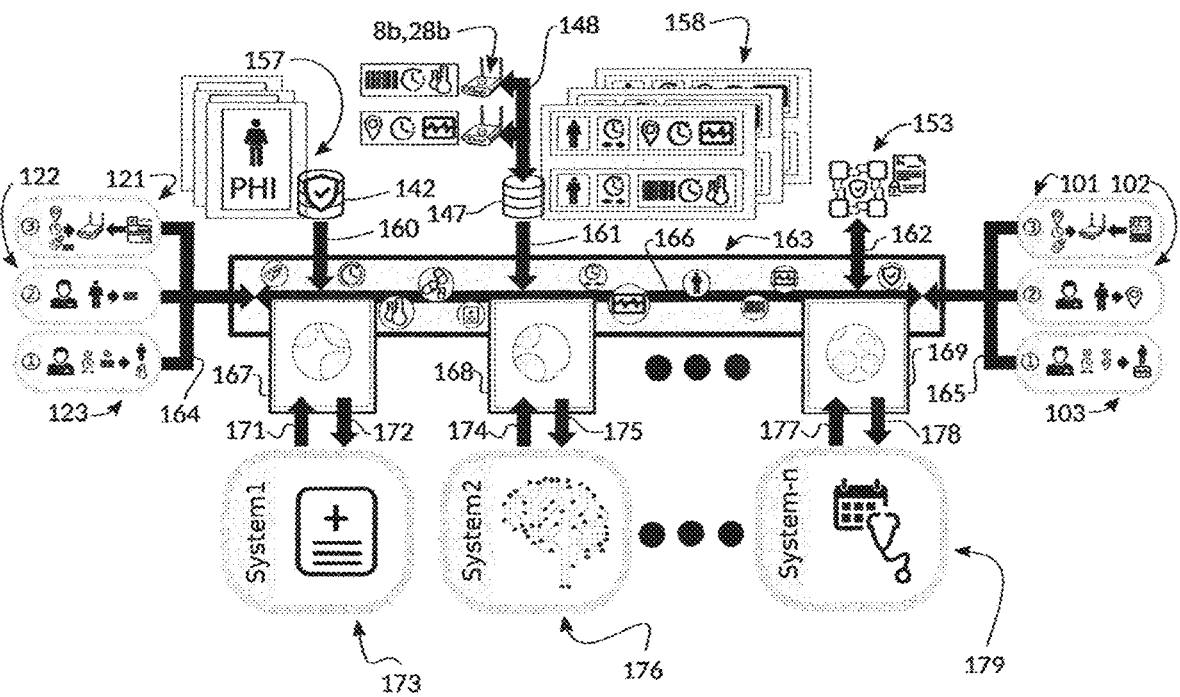
FIG. 9 is an illustration of the details of the third layer of a MDGS, data extraction and export, in an embodiment.

The third layer of the Medical Data Governance System is data extraction and single point of truth for legacy and future healthcare data systems. As depicted in FIG. 9, dependencies for adequate data outputs are defined as follows: the database 147 is populated with multiple 158 patient associated data session records 145, and the different PHI data 157 are also recorded and protected from non-authorized use 142 and interfaced to the MDGS 160. A Block Chain external service 153 is used to prevent data tampering and interfaced to the MDGS 162. Real time data is available through secure proxy tunnel 148 from bedside MDDS systems 8b, 28b. Previous location and proper time reference, metadata drivers and medical device drivers are set and ready 101. Drivers for barcode or POC inputs are properly installed to the MDDS system 8b, 28b, connected to laboratory, spot-like, multi patient medical systems 121. Patient ID is coded to barcode or POC patient code from third party systems and is available for research 122. Patient locations are available from third party systems or documented 102. Active healthcare professional(s) or an adequate automated system is assigned to verify and confirm patient id, location or barcode ID, time span, and to validate the collected data 123, 103.

True Source of Data and Data Export

As depicted in FIG. 9, by concentrating all available medical relevant data into a single source designed to handle very large, different data formats (data, metadata, values, trending, waveforms, video etc.) and providing a subset of data to each receiving subsystem 173, 176, 179 with the correct source and time reference, the Medical Data Governance System becomes the True Source of Data and guarantees the data consistency through the use of block chain signatures.

Due to the exponential data availability from growing health related devices, the risk of data not being collected, or worst being wrongly associated grows exponentially. The Medical Data Governance System opposes this trend by using the same data to augment the data affinity and isolate and indicate a possible association or data integrity errors.

An MDGS 163 data export subsystem with specific, recorded, and real time data in relation to location or to patient source can be configured 167, 168, 169 for an output system 173, 176, 179. Internal to a MDGS export data sub-item, a backbone of all data is available 166 for export drivers 167, 168, 169 access. For example, a minute-based representative value subset for a patient can be configured (exported to EMR, along with the triplets Unique Identifiers (IUD) for later more in-depth review 173, 176, 179 through a different export driver. Selected high frequency, high accuracy data can be exported, after a prolonged period like 30 or 60 days, to AI systems for machine learning processes 173, 176, 179.

In essence, data export of the same complete data acquired from medical devices, including tethered wearables via their Bluetooth descriptor, 167, 168, 169 can be different depending on the different requirements of exporting systems, and the export drivers and protocols 171, 172, 174, 175, 177, 178 can be created on demand from original, complete, high frequency, high fidelity, rich data sets originated from Digital Black Box and stored in MDGS records, time synchronized and with positive patient identification and data validation.

As mentioned above, data from patient wearables can be transmitted directly to a specific local MDDS 8a for further processing in accordance with the various methods of the invention. However, a patient roaming within or about a facility with a wearable will not have their data captured when they are out of range of any MDDS 8a receiver. Accordingly, any data generated by a roaming patient will be lost, as the wearables have only a limited storage capacity. Furthermore, there are no other commercially available Bluetooth bridges to connect Bluetooth wearables to the hospital EMR.

Figure 10:
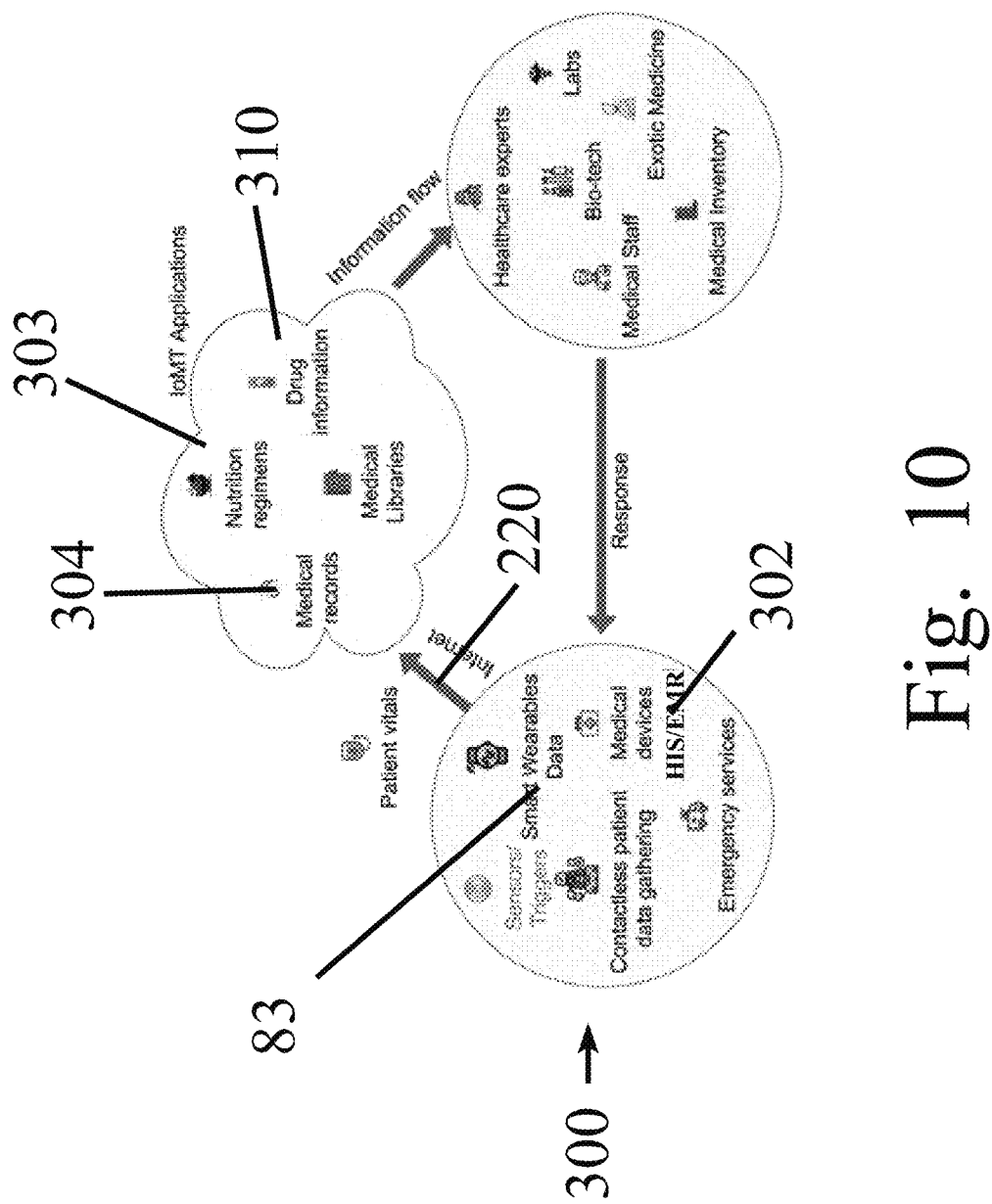
FIG. 10 is an overview of an embodiment of the invention illustrating data flow from wearables to the EMR.
Figure 11:
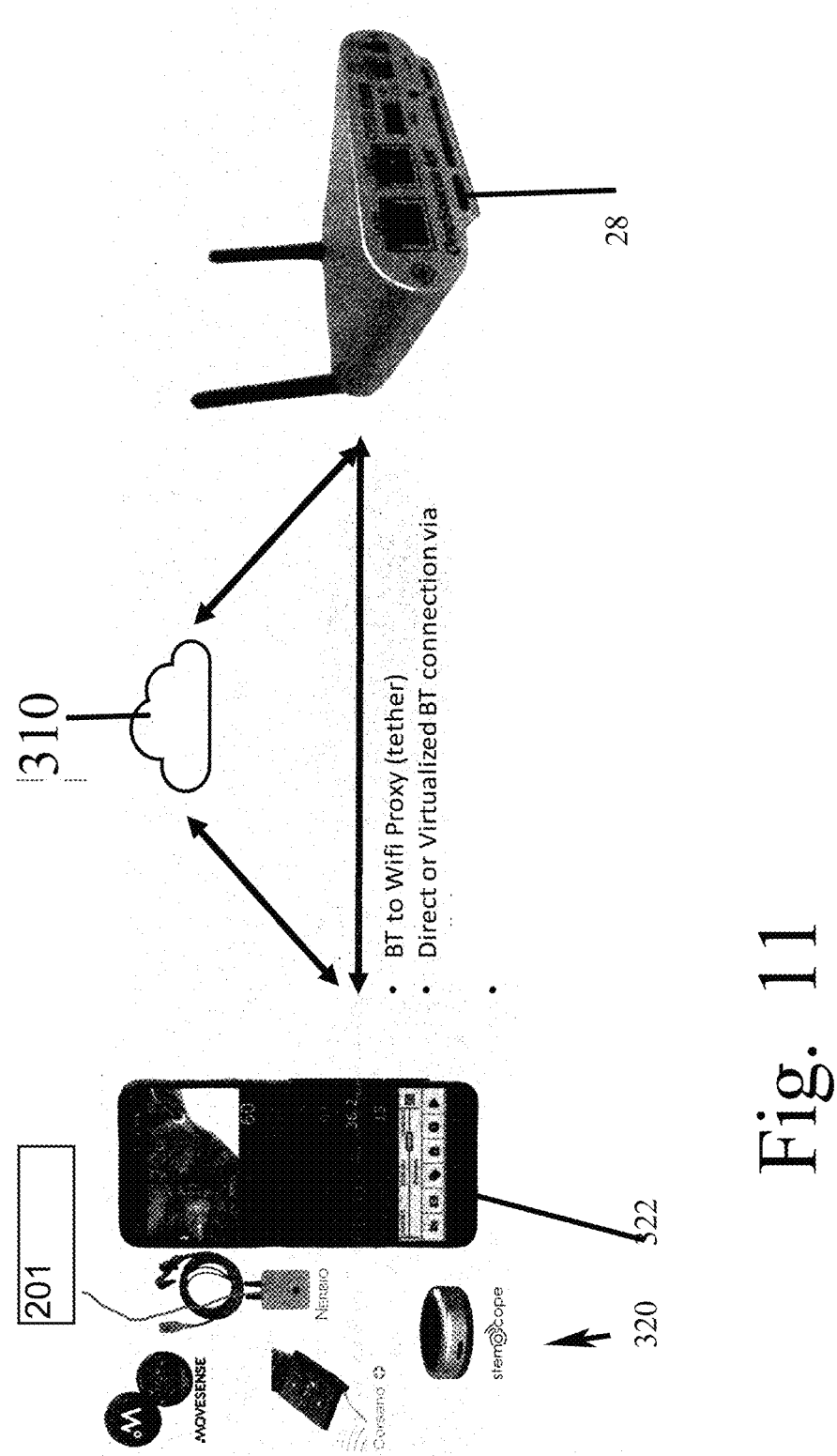
FIG. 11 is an overview of the embodiment of obtaining data from patient wearables within a facility.

Referring now to FIGS. 10 and 11, diagrammatic illustrations of an embodiment of the invention is shown. The illustration shows a mesh network using various smart devices (204, 206, etc.) to function as virtual nodes to transfer data from wearables 202 to the EMR using the methodology of MDG as described above. In accordance with the inventive concept, a novel Bluetooth proxy network is provided. The network is a virtual and distributed proxy network. This network uses the closest Bluetooth host (receiver) and tethers the connection between the wearable 202 to a central MDDS unit 28 device via Positive Patient Identification methodologies as discussed above and explained in further detail below. The central MDDS unit 28 sends the data to the EMR. Across the entire proxy network MDDS unit 28 constantly searches for better connections for each wearable 202 on the proxy network, based on signal strength as determined by the various nodes in the system, and then disconnects the old connection and establishes the new connection. A key part of the invention is that any computing device (e.g., any smartphone, tablet, computer, smartwatch, and IoT device) in the facility with Bluetooth capability can have a proxy application actively installed that makes the device a node of the proxy network. The proxy application can be downloaded from, e.g., an internet accessible server in the well-known manner to any tablet, computer, smartwatch, and IoT device within or about a healthcare facility, the application enabling the tablet 203, computer 206, smartphone 204, or IoT device to become a virtual router capable of sending data from the wearables 202 to the central MDDS 28. The proxy application may also be downloaded to the smartphone 200 of the patients. Each patient with a wearable 202 can thus become part of this virtual, distributed proxy network, and have data from the wearables 202 directly or indirectly (via the smartphone) relayed to the MDDS 8a, 28, using the tablets, computers, smartwatches, and IoT devices, etc., as intelligent proximity sensing virtual routers. Thus, every computing device in the facility including smartphones 200, tablets 203, computers

206, smartwatches and IoT devices, are actively transformed into Bluetooth hotspots and are individually converted into proxy devices, collectively working to create a virtual proxy network that seamlessly connects with the central Medical Device Data System (MDDS) 28 unit that sends the collected data to the Electronic Medical Record (EMR) and MDGS. The inventive proxy network can be effectively range extended by using LoRa technology as explained in more detail below. The continuous searching and switching of wearable devices 202 among these Bluetooth hotspots enhances the reliability of data transmission, forming an intelligent routing system. The intelligent routing system ensures the seamless continuity of data from the patient by continuously searching for the best Bluetooth signal strength amongst the computing devices in the facility. An advantage of the inventive system is that a patient can roam the facility with wearables 202 not paired to a specific smartphone 200, pairing and unparing with virtual nodes in the system based on proximity.

A patient's smartphone 200 may optionally be paired with one or more wearables 202 in the well known manner so that data from the all of the patient's wearables 202 may be transmitted to the smartphone 200, the smartphone 200 then acting as a dedicated mobile virtual node when the patient is roaming. Pairing the patient's phone is, however, mandatory when monitoring remotely, i.e., away from the facility, as will be described in more detail below. Each MDDS device 8a shares the Bluetooth Descriptor of every Bluetooth medical device, including patient wearables 202. The list of Bluetooth Descriptors on the various virtual nodes of the system is populated, and continually updated by the central MDDS unit 28. Participating smartphones 204 and computers 206 (i.e., smartphones 204 and computers 206 that have the proxy application downloaded and installed) which may be mobile or stationary devices, can form virtual nodes of the inventive proxy network, the nodes operating to relay data from wearables 202 to the central MDDS device 28. By way of a non-limiting example, the smartphones 204 may be those carried by healthcare professionals within the facility, and the computers 206 may be desktop or laptop computers positioned throughout the facility in individual offices. Each participating smartphone 204 or computer 206 has the proxy application installed thereon, the application also allowing communication between the patient bedside MDDS devices 8a, with the central MDDS device 28 storing and sharing the Bluetooth Descriptors of every wearable 202 in the facility. As is known in the art, the Bluetooth Descriptor is a MAC address of the Bluetooth device, or a serial number of a device, or any unique identifier of a device. Thus, when any patient wearable 202 is within Bluetooth range of either an MDDS device 8a or a participating smartphone 204 or computer 206 (i.e. a virtual node as defined above), the data from wearables 202 may be transmitted to the central MDDS unit 28 for further processing. It should be noted that the MDDS units 8a, 28 do all of the data processing of the signals from wearables 202, with the patient phones 200, smartphones 204, and computers 206 simply serving as physically distributed (and sometime mobile) virtual nodes to relay data from wearables 202 roaming in or near a health care facility. It should also be noted that the central MDDS (also central server) unit 28 sends the signals from wearables 202 such that some signals will be processed and transmitted to, e.g., an EMR system for storage or transmission to a health care provider. While the present invention is described in the context of the MDGS environment, it can be readily appreciated that the method, with few or no modifications, can be practiced in any scenario where multiple Bluetooth enabled devices are distributed in a given facility or local area.

As has been mentioned, the central MDDS unit 28 and all proxy computing devices or virtual nodes store a list of Bluetooth Descriptors. The list can be generated using multiple methods as would be apparent to one of skill in the art. For example, an NFC chip or sticker can be attached to one or more wearable Bluetooth devices 202. A health care worker can associate the device 202 with a particular patient using the NFC reader in their mobile phone 204, the phone 204 positioned to scan a patient bracelet with identifying information such as the patient's name, barcode, etc. thereon. The application on the phone 204 will read the patient's medical record number from the bracelet and confirm the identity and bed location in the facility ADT (Admitting, Discharge & Transfer) database. The local MDDS 8a will then associate the patient's medical record number with the wearable 202, and pair the wearable 202 to the bed location and associated IoMT gateway at the patient's bedside. The Bluetooth Descriptor will then be added to the active list of Descriptors in the facility stored on the central MDDS unit 28, and then the updated list of Descriptors are pushed to the computing devices and MDDS devices 8a on the proxy network. As the patient roams the facility, any MDDS 8a, 28, phone 204, or computer 206 within Bluetooth range of the patient will automatically detect the patient's wearable 202, disconnect the existing connection, pair with it, and begin receiving (raw) data therefrom. Conversely, as the patient roams the facility, any node such as MDDS unit 8a, phone 204, or computer 206 that is about to lose connectivity to a wearable 202 due to a weak signal, will preemptively disconnect, to avoid possible data loss (from the wearable 202) from loss of signal detection. It should be noted again that the smartphones 204 (or laptops, tablets, etc.) of hospital/healthcare facility workers (doctors, nurses, administrators) would act as roaming virtual nodes when running the downloaded proxy application, this action effectively expanding the effective range of the inventive method. Reconnection of the wearable 202 to another virtual node is relatively fast, milliseconds versus minutes. The central MDDS unit 28 will determine whether to process, discard, or retransmit the data from a virtual node to, e.g., an EMR system.

In operation, central MDDS unit 28 monitors all of the virtual nodes created by smartphones 204, computers 206, etc. to determine the signal strength of all of the wearables 202 in the facility. The central MDDS unit 28 sends control signals to the virtual nodes to effect pairing and unpairing of the virtual nodes with wearables 202 based on the signal strength and proximity of the wearables 202. The central MDDS unit 28 will send data from the wearables 202 to an EMR for storage or further processing. The Bluetooth peer-to-peer communication scheme described above, when utilized within a local network is inherently secure due to its limited range, requiring physical proximity for unauthorized access. This dual-layered defense strategy not only safeguards Bluetooth peer-to-peer connections within the local network but also provides an additional shield against potential external cybersecurity risks, creating a comprehensive and secure infrastructure for seamless communication.

The inventive system may also be implemented using LoRa technology. This will allow long range monitoring of wearables 202. In this scenario, the proxy device, patient smartphone 200 with the aforementioned proxy application installed thereon, transmits wearable data through a LoRa phone accessory 201. A RFM95W LoRa transceiver or equivalent may be used for this purpose, or any other equivalent device as is known by those of skill in the art, the transceiver 201 may be built into the phone 200 or added as an aftermarket accessory. The proxy application already installed includes instructions for operating the accessory 201 as a node in the LoRa network of the invention as will be described below. The proxy application may also download the list of wearable identifiers as discussed above to the phone 200 so that the phone 200 can associate one or more wearables 202 to a specific patient when the wearables are paired directly to the phone. The data from the wearable 202 is transmitted to the phone 200 in the usual manner. The LoRa accessory 201 transmits data from the LoRa enabled phone 200 using cellular or Ethernet technology. The receiving side, e.g., a hospital EMR for example, receives sent data using cellular or Ethernet technology. Using this technique, when a patient leaves the hospital with a wearable paired phone 200, the obtained biometric data may be transmitted over long distances using LoRa technology. Patient data from wearables 202 can be monitored and transmitted to MDG via the phone 200 in real time so that, e.g., any emergency can be immediately detected.

Dynamic Mapping, often referred to as dynamic routing, is the process of continuously determining the most effective path between two endpoints by evaluating various available modes of connectivity and adjusting the route as conditions change. This involves real-time or near real-time analysis of multiple factors—such as traffic flow, network load, geographic constraints, and multimodal transportation options—to ensure that the chosen path remains optimal. In essence, dynamic mapping enables systems to adapt on the fly, selecting or recalculating routes based on current conditions, resources, and connectivity alternatives. As discussed above, there are scenarios where data from a Bluetooth connected wearable 202 cannot directly reach its final destination via a Bluetooth network alone. Instead, it must be relayed through a series of (non Bluetooth) connectivity segments. The present invention uses a novel dynamic mapping scheme as described in detail below.

In the scheme of the present invention a LoRa network formed of geographically distributed wearables 202 paired with a LoRa enabled smartphone 200 is used to create a series of connectivity segments, the connectivity segments determined in accordance with the inventive scheme. Wearable data is first sent from a Bluetooth enabled wearable 202 to an intermediate device (in the present case smartphone 200 as discussed above) that utilizes LoRa, then potentially forwarded through another LoRa node, and finally passed from LoRa to an EMR via, e.g., an MDDS device equipped to receive LoRa transmissions. If the wearable 202 is recognized by the Bluetooth proxy network as described above, i.e., its descriptor is in the list of descriptors, it may rejoin the proxy network once within range of a virtual node, so that when a patient returns to the facility his wearable 202 can automatically reconnect to the proxy network and begin transmitting data. The Lora device 201 attached to phone 200 may then manually be disconnected but preferably, this is done automatically by way of the downloaded proxy application using techniques as would be apparent to one of skill in the art. Likewise, when a patient is outside of the range of any nodes in the mesh network, the LoRa device 201 under control of the downloaded application, can automatically establish itself as a node in the LoRa network.

The present invention uses dynamic mapping of LoRa nodes in a LoRa network to continuously assess all possible paths for a LoRa data transmission—evaluating current signal strengths, network congestion, and available relay points—before determining that the optimal route involves bridging from Bluetooth to a LoRa enabled phone 200, going through one or more LoRa nodes, and then transmitting directly to, e.g., a LoRa equipped MDDS. As conditions change, dynamic mapping would automatically reevaluate these routes, potentially identifying a more efficient or reliable path to ensure data delivery.

Figure 12A:
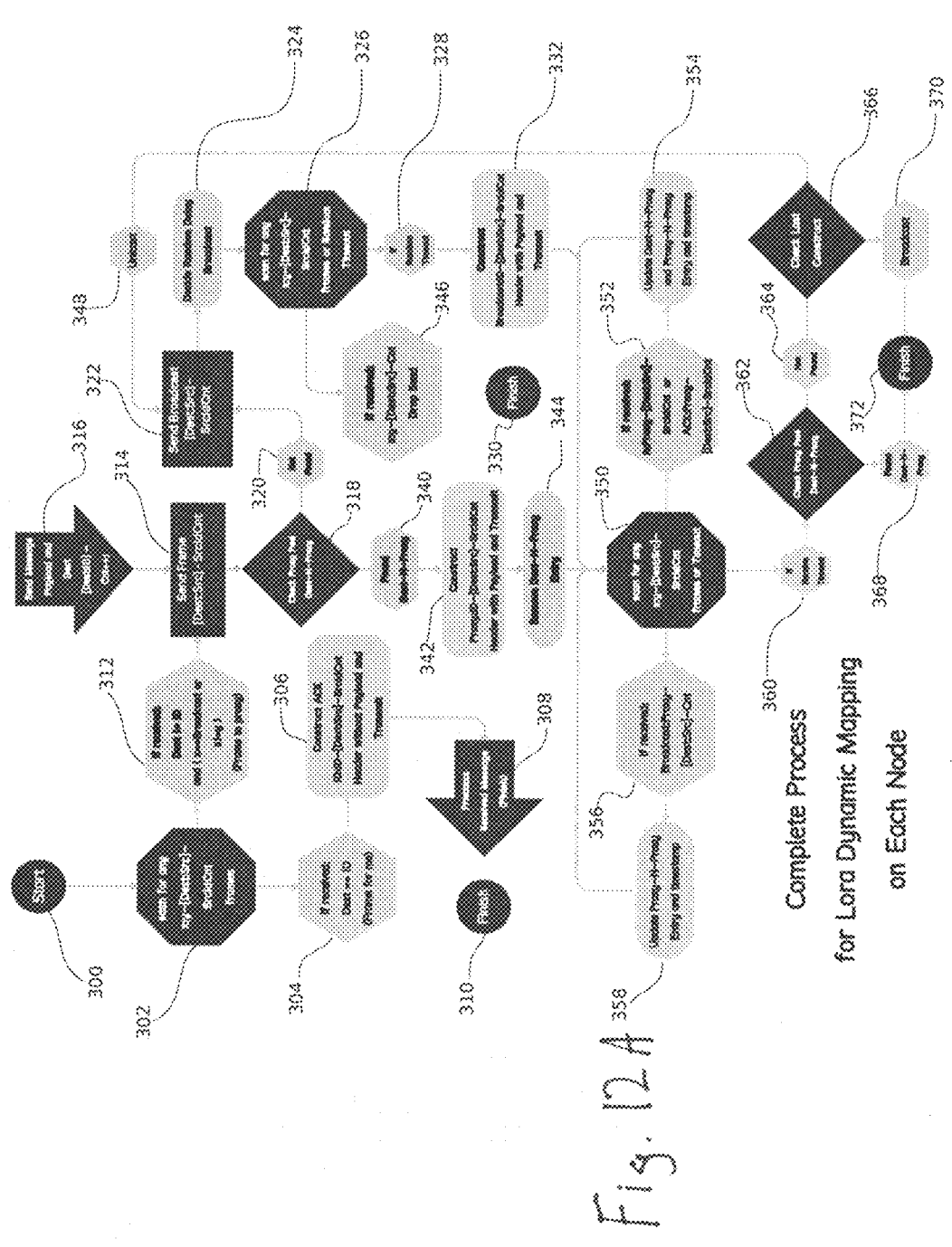
FIG. 12A is a flowchart detailing the LoRa dynamic mapping process of the invention.

Referring now to FIG. 12A and B an operational flowchart and associated message frame of the LoRa network formed of LoRa enabled wearables 202 are shown and described. As stated above, a node in the network is formed by pairing a wearable 202 to a LoRa enabled smartphone 200. Other methods of networking wearables 202 using LoRa technology may be used as would be apparent to one of skill in the art. FIG. 12A is a flowchart illustrating the dynamic mapping scheme of the inventive LoRa network, focusing on the decision making process of a single node, the node designated as the current node or just node for purposes of the discussion.

This flowchart, labeled with states 300-372, shows how a LoRa node in the inventive network:

1. Listens for incoming frames (radio messages).
2. Forwards or delivers messages to upper layers (e.g., a connected phone 200).
3. Discovers routes dynamically, deciding whether to broadcast or use a known unicast next-hop or connectivity segment.
4. Retries or confirms deliveries using ACK frames or by observing broadcasts from peers.

Because multiple transmissions can happen concurrently, the node may be in more than one pass through or run of the flowchart at the same time, each with its own random delay or waiting for ACKs.

Figure 12B:
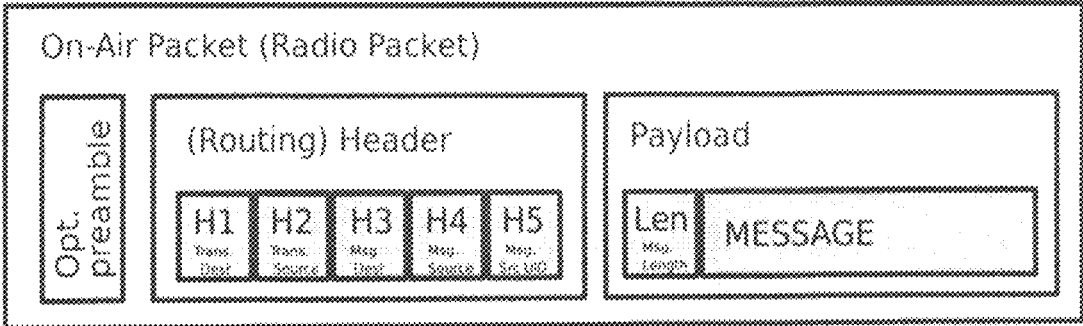
FIG. 12B shows message frames used in the LoRa network of the invention.

The on air packet format is shown in FIG. 12B and described below.

Header Structure and Notation

The header structure and notation used with the message frame of the inventive scheme is now described. Every LoRa message has a 5-element header (H1, H2, H3, H4, H5) plus an optional payload (i.e., the data from the wearable 202):

H1=Transmitted Destination ID (0=broadcast).

H2=Transition (Immediate) Source ID (the node that is actually sending the frame at that moment).

H3=LoRa ID of the intended final destination (the ultimate target).

H4=LoRa ID of the original source (the node that originated the message).

H5=Message counter, unique per (H4) for some time window. E.g., 32 bits can ensure uniqueness for hours if a node sends 100,000 messages.

Hence, we can use the following shorthand for the header: H1,H2-[H3,H4]-H5. The shorthand used in the flowchart is written as: [Dest, Src]-SrcCnt (message counter), which corresponds to (H3, H4)-H5, plus the immediate fields (H1, H2).

As stated above, each LoRa message begins with a 5-element header that helps the network determine how to forward (proxy) the message to its final destination. The header fields described in detail are:

1. H1—Transmitted Destination ID

Identifies the immediate destination for this radio hop, i.e, the connectivity segment.

If H1=0, the message is broadcast (i.e., intended for all nodes in range).

If H1*0, then it indicates a specific node ID for unicast.

2. H2—Immediate Source ID

The ID of the node currently transmitting the message. Typically set to "my Node ID" when this node sends. Thus, node one will have a node ID of 1.

3. H3—Ultimate (Final) Destination ID

The LoRa ID of the node that should eventually receive the payload.

This is known at the time the message is created by the upper layer (the LoRa enabled smartphone 200) that is a node in the system.

4. H4—Original (Final) Source ID

The ID of the node that originally created the message.

5. H5—Message Counter

A per-node counter (unique in combination with H4) to identify the message.

Ensures messages can be distinguished even if broadcast or retransmitted across multiple hops.

Payload

1. After the header, each message contains a payload.
2. The payload has:

A length field (describing how many bytes of actual message data follow).

The message data itself.

Example: Header (H1, H2, H3, H4, H5)+Length (1 byte or more)+Payload data.

3. An optional preamble might be any other data to identify the transmission frame version, beginning, or the elements of the standard radio transmission identifiers, including checksum or other data safety elements as known in the art.

Node ID Allocation

Each LoRa node is assigned a unique ID (an integer).

ID=0 is reserved for broadcast. Hence no actual node will claim the ID 0; it exists only to indicate a broadcast destination.

All valid node IDs (i.e., actual nodes) are integers>1. (Sometimes ID=1 may be used for a special or gateway node, but that depends on the network design.)

Broadcast vs. Unicast

When H1=0, the message is considered a broadcast, meaning all nodes in range should process it.

When H1≠0, it is a unicast to a specific node ID.

Because H3 is the ultimate destination ID, a unicast typically sets H1=next Hop ID (where the "next Hop ID" is a connectivity segment which is either the final destination itself or an intermediate forwarder).

ACK Messages

ACK messages are used to acknowledge receipt of a message and contain no payload.

Therefore, the payload length=0.

In the typical scheme, an ACK is sent "to itself" in the sense that the node sets:

HI=the same node ID (so "transmitted destination" is itself).

H2=the same node ID (immediate source is also itself).

This might appear as (H1=(node) ID, H2=(node) ID, [H3, H4], H5), with H3=ID (the node ID of the final destination) and H4 being the original source from the incoming message, plus the counter H5.

So, we have for the original message and the ACK message the following notation:

Original message: (H1, H2, [H3, H4], H5, payload), where H3=final Destination ID.

ACK message: (H1=ID, H2=ID, [ID, originalSrc], originalH5, payload Length=0).

In simpler terms, an ACK's only purpose is to confirm receipt, so there is no message data or payload, the node just reuses the unique (H4, H5) from the original message to let the sender or forwarders know which message got acknowledged. Note that H3 will also be identical to H1 and H2, but
to recognize the ACK it's enough to check if the H1 equals
H2.

The flowchart in FIG. 12A can now be described, from
Start 300 through various branches to final "Finish" states
310, 330, and 372, the flowchart using the message frame
shorthand as described above. Of course, each and every
node in the LoRa network will process messages in accor-
dance with the flowchart process described.

State 300—Start/Idle

The current LoRa node is idle, waiting for incoming
frames on the radio interface in which case it proceeds to
state 302. If the node receives data from an upper layer
(LoRa enabled smartphone 200, app, etc.) requesting a new
message to send the node goes to state 316.

State 302—Scan for Any [Dest=Src]-SrcIdCnt Frames

In state 302 the node is continuously listening for new
LoRa frames. When a frame arrives with a header [x,
y-(Dest, Src)-SrcCnt], the node checks whether:

1. The transmitted destination (H1=x) matches this Node
ID (i.e., the current node is the destination) or is
broadcast (=0).
2. The ultimate destination (H3=Dest) and ultimate source
(H4=Src) are relevant.
3. The node is in some other special state (e.g. waiting for
an ACK or broadcast from a neighbor).

Depending on the content of the received header, the node
goes to:

1. State 304 to check if Dest ID=this Node ID.
2. State 312/314 if the message is for someone else
(retransmit queue).
3. Or a "continue listening/ignore", i.e., stay in state 302
if the message is not relevant to any active process.

State 304—Is the Message Addressed to This Node?

1. If Dest=ID (i.e., H3 is the current node's ID), then we
have "a message for the current node."
2. If yes, continue to state 306. Otherwise, the flow goes
toward 312 (message is for forwarding) or is ignored if
no match.

State 306—Construct ACK

Because the message is indeed for this (the current) node,
the node constructs an ACK frame without payload. The
ACK header typically sets:

H1=ID (transmitted destination=current node ID; effec-
tively telling the original or the previous node it is the
final target).
H2=ID (current node as the immediate source).
[H3, H41 is [ID, Src] from the received header.
H5=the same counter SrcIdCnt from the received mes-
sage.

This ensures the original transmitter (or any forwarder)
recognizes that the destination node has successfully
received the payload.

State 308—Process Received Message

Deliver the payload to upper layers (e.g., smartphone
200).
Since the node has constructed and sent an ACK (in 306),
the node has completed this "run."
Next, go to 310—"Finish."

State 310—Finish (Received Message)

End of this receive run.
The node can return to Start (300) or remain in the idle
loop for further receptions.

State 312—Message for Another Node

This is the branch where the received message is not for
this node and is not an ACK for this node:

(Dest!=current Node ID), and (x!=0) or (x!=y), mean-
ing it is neither a broadcast for this node nor an ACK.
This message can be queued for retransmission because
the node acts as an intermediate.
Move on to 314.

State 314—Enqueue/Send Frame

Places the message in the transmit queue, preserving (H3,
H4, H5).
Or, if this is a new message from upper layers (coming
from state 316), it constructs (H3, H4, H5) from the
upper layer input.
In either case, the node will figure out how to forward the
message (unicast or broadcast). That logic is in 318.

State 316—Input From Upper Layer

A connected phone/application wants to send data to some
other LoRa node with ID=H3 (Dest).
The local (current) node sets:
H3=destination ID (final recipient's ID).
H4=my Node ID (original source).
H5=next Local Counter (unique ephemeral counter).
Pass the half-constructed frame (header+payload) to the
queue in 314.

State 318—Check Proxy Pool (Dest→N→Proxy)

The node checks an internal routing/"proxy" table for
(H3→next Hop ID).
If an entry is found—Go to 340 (Unicast).
If not found—Go to 320 (Broadcast).
This proxy table is managed at states 342, 344, 350, 352,
354, 358 as discussed below.

State 320—Not Found→Broadcast

If no known next-hop is found for the final H3, the node
decides to broadcast.
Move to 322 to build and send a broadcast frame.

State 322—Send Broadcast [Dest: Src]—SrcIdCnt

The node constructs a broadcast frame:
H1=0 (broadcast).
H2=current Node ID (immediate source).
Retain H3, H4, H5 as set by upper layer or from the
message being forwarded.
Include the payload.
Next, proceed to 324 (random delay).

State 324—Decide Random Delay for Broadcast

To reduce collisions if multiple nodes attempt the same
broadcast, the node picks a random delay (e.g., 2-100
ms).
The node checks if the message is already heard during
this delay in 326.

State 326—Scan for Identical [Dest: Src]-SrcIdCnt] or Wait
for Timeout

The node keeps listening for any identical message (H3,
H4, H5) from neighbors.
If it hears a broadcast (state 346), it skips sending because
another node broadcasted it successfully. Then it jumps
to 330—one of the "Finish" states.
If no identical message arrives before the delay ends (state
328), the node proceeds to send the broadcast.

State 328—Random Timeout

The random delay has elapsed, and no identical message
was detected.
Move on to 332 to actually transmit the broadcast.

State 330—Finish (Skip Broadcast)

Since another node already broadcasted the same (H3,
H4, H5), the node does not send.
This broadcast run concludes here.

State 332—Construct Broadcast Header with Payload & Transmit
Final step of the broadcast. Transmit the frame:
H1=0 (broadcast), H2=current node ID, [H3, H4], H5, plus payload.
Then the node enters the "post-transmit" wait state 350 (to see if it receives an ACK, a resend request, or hears another broadcast that might help route discovery).
State 340—Found Next Hop—Unicast
The proxy table indicated (H3—next Hop ID).
That means the node can unicast the message, so it moves to 342.
(Note: State 348 in the diagram is simply labeled "Unicast," often near 340. It confirms the choice to do a unicast instead of a broadcast.)
State 342—Construct Unicast Header & Transmit
Build the unicast frame:
H1=next Hop ID (the known next-hop from the proxy table).
H2=current Node ID.
Keep [H3, H4]-H5 from the original.
Send the frame with payload.
Then call 344 to remove the proxy entry.
(Removing the entry ensures that if no ACK is received, the node will default back to broadcast next time.)
State 344—Remove Dest→N→Proxy Entry
Removes (H3→next Hop ID) from the table.
Next, the process transitions to "post-transmit wait" in 350.
State 346—If Received [x, y (Dest, Src)-Cnt]=>Drop Send
This is the event occurring during the random delay (326).
If the node hears an identical message, it does not send.
Then go to 330 (Finish).
(See state 346 in the diagram, which specifically triggers the drop/bypass of sending.)
State 350—Post Transmit—Wait for ACK or Resend or Broadcast
After sending either broadcast or unicast, the node listens for 100-200 ms for:
ACK frames from the final destination, or
Broadcast from another node carrying the same (H3, H4, H5), or
Unicast from an intermediate that might confirm a route.
During this time, we might see:
State 352 if an ACK or unicast is received, or,
State 356 if a broadcast route is discovered.
State 352—If Received nProxy-[Dest: Src]-SrcIdCnt or ACKProxy-[Dest: Src]-SrcIdCnt
The node recognizes a returning unicast or an ACK from the next-hop or from the ultimate destination.
Moves on to 354 for updating the proxy table.
State 354—Update Dest→N→Proxy and Proxy→N-→Proxy Entry and Timestamp
The node knows that "to reach H3 (Dest), I can forward through H2."
Creates or updates the table entry (H3→H2).
Also note that receiving from H2 means there is a forward link from that node as well.
Refresh timestamps so the route remains valid for some period.
State 356—If Received: BroadcastProxy-[Dest: Src]-Cnt
Another special case: we heard a broadcast that told us there is a route (or a node) for (Dest, Src).
Moves on to 358 to update the proxy or any local link data.

State 358—Update Proxy→A→Proxy Entry and Timestamp
Similar to 354, except specifically for a broadcast scenario:
Possibly sets (ID→ID) if the current node is the same node, or
Recognizes that the broadcasting node can be a next-hop (connectivity segment) for future messages.
Time-stamp or "last-heard" refresh.
State 360—Receive Timeout
The waiting period (100-200 ms or so) has expired. The node then checks to see if the route is found or not.
State 362—Check Proxy Pool Dest→N→Proxy
After the waiting window, does an entry (H3→some NextHop) exist now?
If found go to 368.
If not found go to 364.
State 364—Not Found
No route was discovered. Check if a unicast or broadcast was previously attempted.
State 366—Check Last Construct
If the last attempt was unicast and the node failed to get an ACK or broadcast, it can try a fallback broadcast. Or vice versa.
If it was a broadcast attempt that also failed, the node might do repeated broadcast or eventually give up.
State 368—Found Dest→N→Proxy
There is a valid route or it is discovered that the final destination got it.
The process can "finish" successfully.
State 370—Broadcast
If the unicast route was invalid or not discovered, the node reverts to broadcast.
Go back to the broadcast branch (essentially state 322 again).
State 372—Finish
Concludes the entire post-transmission process.
The node returns to idle or continues other concurrent runs.
The operation of each node in the dynamic mapping LoRa scheme being described with reference to the flowchart of FIG. 12A, some aspects of the inventive scheme are discussed for further clarification with details of operations at several decision blocks.
Concurrency
Multiple "runs" of the above flow can occur simultaneously. One message may be in a random delay as described (see states 324-328). Another may be waiting for an ACK (state 350). Meanwhile, the node keeps listening at state 302. States 302, 326, and 350 are all points where the node is actively scanning for incoming frames, but for different subsets of messages or different concurrency contexts.
Idle Listening and Receiving Data
Starting at Block 300 the node is essentially idle, it monitors the LoRa channel while also awaiting any signals from its upper layers (e.g., a connected phone). At Block 302, when a new incoming message frame arrives, the node transitions to Block 302 to analyze the header, it checks what node the message is intended for (H3=Dest) and what node sent it (H4=Src), plus the immediate sender H2). From here, three main scenarios arise:
1. It's Addressed to the Current Node.
The node sees (Dest=this Node ID) and moves to blocks (304) and (306). It constructs a quick ACK (no payload), sets H1=ID and H2=ID, and reuses H3=ID, H4=Src, H5=SrcCnt from the received message.
Next, it delivers the payload to the upper layer (308) and returns to idle (310), and is done with that message.

2. It's for Another Node

If(Dest!=this Node ID) and it's not merely a broadcast or an ACK relevant to this node, the node transitions to block (312) and queues this message for forwarding at (314).

3. It's Irrelevant or Already Handled

If the node is in special wait states (e.g., random delay at (326) or waiting for ACK at (350)), it might interpret the incoming message differently—possibly discarding duplicates or learning new routes. Otherwise, if the message doesn't match any active process, it's ignored and the node remains ready for the next event.

Throughout all of this, the node loops around (302) to keep checking for new frames whenever it is not actively transmitting.

Sending Data (New Messages)

Upper Layer—(316)

If a connected device (like a LoRa enabled smartphone 200) wants to send a message to "Node X", in this case it is the original source, and the node at idle (300) is alerted, then moves to block (316) to accept the new data. The node builds partial header fields:

H3=destination Node ID (ultimate destination).

H4=Current Node ID (the original source).

H5=a Local Counter (unique for a while).

This new message is placed into the transmit queue at (314), where it gets sorted out for an actual radio send.

Check If Route Is Known—(318)

From the queue (314), the node checks its internal memory (a "proxy table" or "route table" as known in the art) to see if it has a known unicast next-hop for H3. If it finds a route, it flows to (340) for unicast. If no route is found, it flows to (320) for broadcast.

The broadcast path and unicast path are now discussed.

Broadcast Path

If no next-hop is known:

If no next-hop is known:

Decide Broadcast→(320)→(322)

The node sets H1=0 (broadcast), H2=Current Node ID, and retains (H3, H4, H5). The node then prepares the payload.

Random Delay→(324)→(326)

To avoid collisions, the node waits a short random time, continuously listening. If it hears the exact same (H3, H4, H5) message from another node in block (326), it triggers (346)→(330) to skip sending ("someone else broadcast first").

Timeout→(328) & Send→(332)

If no identical message is heard, after the delay the node broadcasts the frame at (332).

Wait for ACK or Resend→(350)

After sending, the node waits for some acknowledgment or a relevant broadcast (350). If it sees an ACK or new broadcast referencing (H3, H4, H5), it may update its route table at (352)/(354) or (356)/(358). If no route or ACK is found before time runs out (360), it checks if it should retry broadcast or revert to idle.

Unicast Path

If the proxy table does indicate a known next-hop:

Use Next Hop→(340)→(342)

The node sets H1=next Hop ID, H2=current Node ID, and keeps [H3, H4]-H5 from the original.

Transmit & Remove Route→(344)

It sends the unicast and then deletes (H3=next Hop ID) from the table. This ensures if no ACK is received, the node won't keep trying a possibly stale link.

Post-Transmit Wait→(350)

As with broadcast, the node waits for an ACK or any relevant transmissions referencing (H3, H4, H5). If none arrive, it might eventually (364)/(366) decide to broadcast instead.

Retransmitting (Proxy) Data

The node may also receive a message that's not ultimately intended for it (i.e., it's for another node), so it steps from (302)→(312)→(314). The process after that mirrors the same broadcast/unicast logic detailed above:

1. Queue the Message for Forwarding (314)

The node retains (H3, H4, H5) exactly so the message's unique ID remains consistent across the network.

2. Check Known Route or Not (318)→(320)/(340)

If the node has a next-hop route in memory, it tries unicast (340). Otherwise, it does the random-delay broadcast approach (320→322→324→326→328→332).

3. Post-Transmit Wait (350)

After sending, the node again listens to see if it receives any acknowledgment (ACK) or an updated broadcast that might help it refine or discover a path.

If an ACK is received from the final destination, the node knows the chain is working. If not, it might eventually revert to broadcast or give up if repeated tries fail.

Throughout these steps, the node may end up at finish points (330) if it detects a duplicate broadcast, or (372)/(368) if it successfully finds a route or an ACK. Meanwhile, it can always revert to the idle loop (300) for new instructions or new receptions. To summarize, each node starts at (300) where it is idle and awaiting an incoming transmission, either a new LoRa frame (302) or new data from an upper layer (316)). If Data Arrives for the node, a quick chain of operations from (302)→(304)→(306)→(308)→(310) handles final delivery and sends an ACK. If Data Arrives for another node, the node goes (302)→(312)→(314). It uses either broadcast route (320)→322→ 324→326→328→332→350) or unicast (340→342→344→350) to forward. If the node generates new data (316) it sets up (H3, H4, H5) then merges into the same forward path (314→318). It either broadcasts (320 . . . ) or unicasts (340 . . . ). After transmitting, the node monitors at (350) for acknowledgments or additional broadcasts that confirm successful delivery or reveal new routes. If an ACK or relevant broadcast arrives (352→354 or 356→358), the node updates its route table. It then checks (360→362→ . . . ) to see if it has established a valid route (368→372) or needs to retry (364→366→370, etc.).

In practice, multiple messages can be in flight; one might be waiting in random delay (326), another might be waiting for an ACK (350), and the node can still get new frames at (302). The design ensures that each message is trackable via (H3, H4, H5), enabling the node to ignore duplicates or glean new routes whenever it sees a relevant broadcast or ACK. In essence, the diagram's blocks depict a flexible, event-driven process where a node listens (300, 302), identifies who a message is for (304, 312), sends or retransmits that message either unicast (340, 342) or broadcast (320, 322), with random delay (324-326), awaits acknowledgments or updated broadcasts (350), updates or discards route entries (344, 354, 358) as it learns or fails to learn next hops, and finally, completes each "run" (330, 368, 372) and returns to idle (300). This loop continues indefinitely, forming a dynamic mapping system that spreads messages, discovers routes on the fly, avoids collisions through random backoff, and confirms delivery via ACKs or broadcast signals.

Final Implementation Notes

Header Fields H1 and H2 change per hop (the immediate sender and immediate receiver), while H3, H4, and H5 stay the same end-to-end, preserving the unique ID of the message so intermediate nodes can detect duplicates or route updates. Delays of 2-100 ms let nodes detect if another neighbor already broadcasted the same message, avoiding collision or duplication. When a node sees a message "for me" (Dest=my ID), it immediately sends a small ACK (no payload). If the original sender (or a forwarder) gets an ACK or sees a broadcast containing the same header, it knows the message is traveling through the network. The node uses (H3-.next Hop ID) entries to do unicast if it learns about a neighbor that can forward to H3. After a successful unicast, that entry is removed. If no ACK or route update is observed, next time the node will revert to broadcast. Timestamps ensure entries expire or are refreshed if they remain valid. Because LoRa transmissions can be slow or spaced out, it's crucial to handle multiple partial transmissions. Each path from Start (300) to a "Finish" state (310, 330, or 372) can take a few hundred milliseconds, and several can overlap.

FIGS. 13A-F, 14, and 15 diagrammatically illustrates the process of sending data from node to node in the LoRa network. The transmission shorthand or notation for the processes as described above is used to denote connectivity segments in the diagrams. Specifically, the notation form:

X, Y [C, D] where X indicates either the operation to be carried out with B indicating a broadcast and A indicating an answer, or the node number of the destination receiver; Y indicates the source of the instant transmission; C indicates the message destination node; and D indicates the source of the message. So B, 1 [5, 1] indicates a broadcast (B) from node 1 (Y) to node 5 (C), the message source being node 1 (D). If node 5 acknowledges by sending an acknowledgment message back through the network it is written as A, 5 [5, 1]. If node 4 transmits the acknowledgment message sent by 5 it is written as 5, 4 [5, 1] which can be interpreted as a message intended for node 5 is acknowledged by node 5, and node 4 is transmitting the ACK. When the acknowledgment finally reaches node 1 from node 2, as is shown in FIG. 15, it is written as 2, 1 [5, 1] which can be interpreted as a message intended for node 5 is acknowledged by node 5, and node 2 is transmitting the ACK to node 1.

FIG. 13A shows the process for transmitting from node 1 to node 125 at time $t_0$, denoted by B,1 [125, 1]. The closest nodes to node 1 are nodes 6-10, all of which receive the broadcasted data packet or frame. The nodes will not immediately retransmit the data, but are programmed with delays to avoid multiply redundant transmissions. The delays are 6-25 ms (milliseconds), 7-55 ms, 8-35 ms, and 10-25 ms respectively for nodes 6, 7, 8, 9, and 10. Node 6 is the first to broadcast and the data is received by nodes 1, 7, and 15. Node 15 is the closest node to node 125, and ultimately transmits the message to node 125 as depicted in FIGS. 13E and 13F. Cancellations eliminate redundancies as described below. Node 1 receives and ignores, node 7 receives but cancels (cancellations are denoted throughout the diagrams by a strike out of the transmission shorthand as described above) its own broadcast as shown in FIG. 13B. Node 10 transmits and node 1 ignores, node 9 receives and cancels it own broadcast, while node 1 receives it and ignores as shown in FIG. 13C. FIG. 13D shows node 8 broadcasting a message (B, 8[125,1]). The message is received by node 12, nodes 7 and 9 which cancel or ignore, and also by node 1 which ignores. Node 15 will transmit to node 125 (destination), and node 125 will send an acknowledgment to node 1 back through the LoRa network as described below. Note that nodes 11, 12, and 15 will start to proxy the message and all the nodes that received it (nodes 6-10) will ignore it as shown in FIGS. 13E and 13F.

Figure 14:
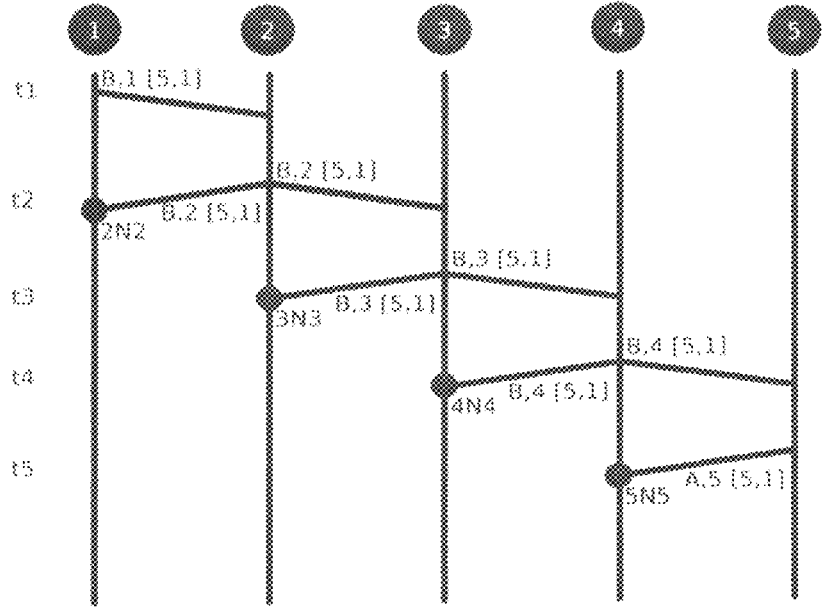
FIG. 14 depicts an example of communication in 5 time cycles in the LoRa network of the invention.

Referring now to FIG. 14, an example of communication in 5 time cycles where node 1 sends a message to node 5 in a 5 node network by proxing through nodes 2,3,4. At time t1 node sends a broadcast to node 5 [1,5]. At time t2 node 2 picks up and resends the message [5,1] to node 1 and 3 and node 3 reads it while node 1 ignores it. At time t3 node 3 picks up and resends [5,1] the broadcast to node 2 and node 4 which reads it. Node 2 ignores the broadcast. At time t4 node 4 picks up and resends [5,1] to node 3 and node 5 reads it, node 3 ignores. At time t5 node 5 picks up, processes the message and returns an ACK. Node 4 adds node 5 to update its proxy list.

Referring now to FIG. 15, the dynamic routing of the inventive LoRa network through 5 message cycles is shown. The shorthand XNY is interpreted as follows:

X is the known destination for the message.

Y is the known routing node for the instant message. Thus, an acknowledgment sent from node 2 to node 1 where node 5 is the destination (that is the node sending the ACK frame) reads 5N2. In FIG. 14, node 1 sends 4 broadcast messages, with the last ACK message setting node 4 to send a last message unicast. Node 1 then sends 3 broadcast messages, and the last message unicast. The ACK message from node 5 sets node 3 to send last unicast for node 5 to 4. Node 1 sends 2 broadcast messages, and the last 2 unicasts. The ACK sets node 2 to send last unicast for node 5 to node 3, node 1 sends 1 broadcast message, and last 3 unicasts. The ACK from node 5 set node 1 to send 1 last unicast for node 5 to 2. Finally, node 1 sends only unicast messages, ACK from node 5 set node 2 to send last unicast for node 1.

FIG. 16 depicts network action when there is a missing node. In the scenario depicted, node 6 and 3 can both receive and transmit from nodes 2 and 4, but node 3 is shut down and is no longer part of the system. [5,1] node 1 sends 4 unicast messages, and since node 5 is known to all nodes; node 1 sends to node 2, node 2 to node 3, node 3 to node 4, and node 4 to 5. The node 2 transmission is not received by node 3 that is not active any more—but node 6 is now active. Node 2 will LOOSE the proxy reference 5N3 and will repeat the broadcast, since it did not 'hear' the node 3 retransmit or ACK. Node 2 resends the broadcast message (to any node listening), and node 6 this time retransmits the broadcast, that will result after 3 more messages as 1-2-6-4-5. Node 6 will pick up and send unicast to nodes 4 and 2. Now 2 knows to send unicast to node 6 and the loop is closed.

FIG. 17 depicts dynamic path preservation when there a message is either not received or not transmitted. Node 1 sends 4 unicast messages, since node 5 is known to all nodes, node1 sends to node 2, node 2 to node 3, node 3 to node 4, and node 4 to 5. If the node 2 transmission is not received by node 3, but it is by node 1, then node 2 will LOOSE the proxy reference 5N3 and will repeat the broadcast, since it did not "hear" the node 3 retransmit or ACK. Node 2 resends the broadcast message (to any node awaiting a message), and node 3 this time retransmits it and node 2 reconstructs the 5N3 proxy reference, and reestablishes the link. Since NODE 3 which node to send the proxy to, it does not enter in delay broadcast state, therefore, the dynamic path will be preserved with more chance than broken (taken by the next broadcasting node). If the node 3 transmission is not received by node 2, but it is by node 4, node 2 will LOOSE the proxy reference 5N3 (an ACK message) and will repeat the broadcast, since it did not 'hear' the node 3 retransmit or ACK. But both nodes 3 and 1 will ignore the repeated broadcast message. The next message node 2 will then broadcast, and node 3 will unicast the message, so the next time node 1 will lose the proxy reference (5N2) and will broadcast the message and reestablish the unicast to node 2 after node 2 will unicast the message to node 3.

FIG. 18 depicts network action when a unicast has not been received. Only four scenarios can happen, designated as A-D in the diagram. In the scenario, node 1 has sent a unicast to node 2 for a message to be sent to node 3 but node 2 does not receive it. In this case we have:

A: [3,1]—node 1 sends Broadcast and node 2 sends unicast; or,

B: [3,1]—node 1 sends a broadcast and node 2 sends Broadcast; or,

C: [3,1]—node 1 sends a broadcast and no node sends or resends the message; or,

D: [3,1]—node 1 sends a broadcast and node 3 replies with an ACK.

Wi-Fi HaLow can also be used to extend the range of the wearables 202. Wi-Fi HaLow enables longer range than many other IoT technology options and provides a more robust connection in challenging environments where the ability to penetrate walls or other barriers is an important consideration. Thus, a patient with a wearable 202 and with a smartphone 200 with a Wi-Fi Halow capability can connect to any network and transmit data to MDG for storage and to the EMR.

As is apparent to one of skill in the art, some data may be lost from wearables 202 during the above-described switching process. In order to limit data loss from the wearables 202, the central MDDS 28 monitors data from all wearables 202 to determine if there is a data gap. Since all wearables 202 have at least a limited storage capacity, upon detection of a data gap, the wearables can be polled by the MDDS 28 via the virtual nodes 204, etc., to fill in lost data. If it is determined that a particular wearable 202 has a data gap, MDDS 28 will initiate transmission of the stored (missing) data from the wearable 202 upon reconnection with the proxy network via the nearest node as described above. The lost data retained in the wearable 202 can then be transmitted time synchronized and inserted into the data stream from the particular wearable 202 determined to have a data gap under control of the MDDS 28, which then transmits the complete and time synchronized data from the wearable 202 to the EMR, so that the data received by the EMR has essentially no gaps.

Although particular embodiments have been described in this disclosure, many other variations and modifications will be apparent to those skilled in the art. Thus, the instant invention can be defined and limited only by the claims to be associated with this application.

What is claimed is:

1. A method for providing long-range, patient-identified connectivity between one or more wearable health monitoring devices and an electronic medical record system, the method comprising:

providing, for a patient, at least one wearable health monitoring device configured to measure physiological data for the patient;

providing a proxy computing device associated with the patient, the proxy computing device comprising a short-range wireless communication interface and a memory;

downloading, from a central medical device data system to the proxy computing device, a list of device identifiers corresponding to wearable health monitoring devices assigned to the patient, and storing the list of device identifiers in the memory;

coupling a LoRa transceiver to the proxy computing device and executing a software application that configures the proxy computing device and the LoRa transceiver to operate together as a LoRa-enabled communication device participating as a node in a LoRa mesh network;

using, at the proxy computing device, the stored list of device identifiers to associate physiological data received from the wearable health monitoring devices with the patient;

receiving, at the proxy computing device, physiological data from the wearable health monitoring devices using the short-range wireless communication interface;

determining, at the proxy computing device and without user intervention, whether the proxy computing device is within a communication range of a facility mesh network comprising proxy computing devices operating as wireless relay nodes within a healthcare facility;

when the proxy computing device is within the communication range of the facility mesh network, transmitting the physiological data toward the central medical device data system through the facility mesh network;

when the proxy computing device is outside the communication range of the facility mesh network, transmitting the physiological data from the proxy computing device through a mesh network of LoRa nodes toward at least one LoRa gateway coupled to the central medical device data system by sending the physiological data in LoRa packets that are forwardable by one or more intermediate LoRa nodes;

and wherein the electronic medical record system receives, from the central medical device data system, patient-specific data based on the physiological data and stores the patient-specific data in an electronic medical record for the patient.

2. The method of claim 1 wherein the proxy computing device comprises a smartphones, a tablet computer, a laptop computer, a smartwatch, a desktop computer, or an internet-connected device configured to execute the software application and to communicate with the wearable health monitoring devices over the short-range wireless communication interface.

3. The method of claim 1 wherein the proxy computing device automatically determines, without user intervention, whether it is within a communication range of a facility mesh network based on at least one of received signal strength, beacon detection, or mesh node availability.

4. The method of claim 1 wherein when the proxy computing device is outside the communication range of the facility mesh network, the proxy computing device operates from a patient residence, outdoor environment, ambulance, or other transport environment and transmits the physiological data through the mesh network of LoRa nodes.

5. The method of claim 1 wherein the LoRa transceivers comprises an RFM95W chipset or an electrically or functionally equivalent LoRa transceiver.

6. The method of claim 1 wherein when the proxy computing device re-enters the communication range of the facility mesh network after transmitting physiological data through the LoRa mesh network, the proxy computing device automatically ceases LoRa-based transmission and resumes transmitting the physiological data through the facility mesh network.

7. The method of claim 1 wherein the central medical device data system updates the list of device identifiers assigned to the patient in response to changes in wearable assignment and redownloads the updated list to the proxy computing device.

8. The method of claim 1 wherein the electronic medical record system receives, via the central medical device data system, LoRa-based messages transmitted through the mesh network of LoRa nodes and parses the messages to extract patient-specific physiological data.

9. The method of claim 8 wherein the patient-specific physiological data contained in the LoRa transmissions includes time-stamped biometric measurements generated by the wearable health monitoring devices, and the electronic medical record system stores the measurements in a time-ordered record associated with the patient.

10. A system for providing long-range, patient-identified connectivity between one or more wearable medical devices and an electronic medical record system, the system comprising:

a plurality of wearable medical devices configured to measure physiological data for respective patients;

a central medical device data system configured to maintain patient-specific device identifier lists and to process physiological data received from facility mesh networks and LoRa mesh networks;

a plurality of proxy computing devices associated with the patients, each proxy computing device comprising:

a short-range wireless communication interface configured to receive physiological data from one or more wearable medical devices assigned to the patient;

a memory configured to store a list of device identifiers downloaded from the central medical device data system; and a processor configured to execute a software application that uses the stored list of device identifiers to associate received physiological data with the corresponding patient;

a plurality of LoRa transceivers respectively coupled to corresponding proxy computing devices, each proxy computing device and its coupled LoRa transceiver forming a LoRa-enabled node configured to transmit physiological data in LoRa packets that are forwardable by one or more intermediate LoRa nodes of a LoRa mesh network;

at least one LoRa gateway communication device configured to receive LoRa packets transmitted through the LoRa mesh network and deliver the packets to the central medical device data system;

wherein, when a proxy computing device is within a communication range of a facility mesh network comprising proxy computing devices operating as wireless relay nodes, the proxy computing device is configured to transmit physiological data toward the central medical device data system through the facility mesh network;

wherein, when the proxy computing device is outside the communication range of the facility mesh network, the proxy computing device is configured to transmit the physiological data through the LoRa mesh network toward the at least one LoRa gateway communication device; and wherein the electronic medical record system is configured to receive patient-specific data from the central medical device data system and store the patient-specific data in electronic medical records for the respective patients.

11. The system of claim 10, wherein the proxy computing device comprises a smartphone, tablet computer, laptop computer, desktop computer, smartwatch, or internet-connected device configured to communicate with the wearable medical devices over the short-range wireless communication interface.

12. The system of claim 10, wherein, when the proxy computing device is outside the communication range of the facility mesh network, the proxy computing device operates from a patient residence, outdoor environment, ambulance, or other transport environment and transmits the physiological data through the mesh network of LoRa nodes toward the at least one LoRa gateway communication device.

13. The system of claim 10, wherein, upon the proxy computing device entering the communication range of the facility mesh network after transmitting physiological data through the LoRa mesh network, the proxy computing device automatically ceases transmission through the LoRa mesh network and resumes transmitting the physiological data through the facility mesh network.

14. The system of claim 10, wherein the central medical device data system is configured to update the list of device identifiers associated with the patient in response to changes in wearable device assignment and to redownload the updated list of device identifiers to the proxy computing device.

* * * * *